(12) United States Patent
Mismar et al.

(10) Patent No.: US 12,059,555 B2
(45) Date of Patent: Aug. 13, 2024

(54) INJECTION DEVICE FOR DRUG DELIVERY AND PACKAGING FOR THE INJECTION DEVICE

(71) Applicant: AMGEN INC., Thousand Oaks, CA (US)

(72) Inventors: Wael Mismar, Redondo Beach, CA (US); Jessica Hai Liu, Agoura Hills, CA (US); Dylan Bourelle, Thousand Oaks, CA (US); Chia-Jung Wu, Redondo Beach, CA (US); Shaun Devitt, Wayne, PA (US); Kenneth G. Schalhoub, Denver, CO (US); Tej Desai, Thousand Oaks, CA (US); Mads Schjoth Due, Redondo Beach, CA (US); Anthony Bitong, Calabasas, CA (US); Arin Keshishian, Sunland, CA (US); Chelsea Balli-Cruz, Winnetka, CA (US); Pierre Burquel, South Weymouth, CA (US); Ryan Oba, Santa Paula, CA (US); Malak Guirguis, Los Angeles, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 17/009,868

(22) Filed: Sep. 2, 2020

(65) Prior Publication Data

US 2021/0060258 A1 Mar. 4, 2021

Related U.S. Application Data

(60) Provisional application No. 63/018,141, filed on Apr. 30, 2020, provisional application No. 62/895,456, filed on Sep. 3, 2019.

(51) Int. Cl.
*A61M 5/31* (2006.01)
*A61M 5/00* (2006.01)
(Continued)

(52) U.S. Cl.
CPC .......... *A61M 5/3137* (2013.01); *A61M 5/002* (2013.01); *A61K 38/179* (2013.01);
(Continued)

(58) Field of Classification Search
CPC ................ A61M 5/002; A61M 5/3137; A61M 5/31501; A61M 5/31505;
(Continued)

(56) References Cited

U.S. PATENT DOCUMENTS 4,664,128 A * 5/1987 Lee ...................... A61B 10/025
401/176
5,607,399 A 3/1997 Grimard et al.
(Continued)

FOREIGN PATENT DOCUMENTS

JP 2018535974 A 12/2018
JP 2018537170 A 12/2018
(Continued)

OTHER PUBLICATIONS

International Application No. PCT/US2020/048975, International Search Report and Written Opinion, dated Dec. 11, 2020.
(Continued)

*Primary Examiner* — Shefali D Patel

(57) ABSTRACT

An injection device is provided, including a syringe having a barrel and a flange and a backstop configured to be coupled with the syringe adjacent to the flange. The backstop includes an inner surface generally extending around at least a portion of the syringe, wherein the inner surface includes at least one protrusion extending away from the inner surface and configured to engage the flange and/or the barrel (Continued)

to permit or promote airflow through a space between the inner surface and the syringe.

27 Claims, 26 Drawing Sheets

(51) Int. Cl.
    *A61K 38/17*     (2006.01)
    *A61K 39/395*     (2006.01)
    *A61M 5/315*     (2006.01)

(52) U.S. Cl.
    CPC ............ *A61K 39/395* (2013.01); *A61M 5/001* (2013.01); *A61M 2005/3139* (2013.01); *A61M 5/31505* (2013.01)

(58) Field of Classification Search
    CPC .. A61M 2005/3123; A61M 2005/3139; A61M 5/001; A61M 2209/06; A61K 38/1379; A61K 39/395; A61K 38/179
    See application file for complete search history.

(56) References Cited

U.S. PATENT DOCUMENTS

| | | | |
|---|---|---|---|
| 5,667,495 A | 9/1997 | Bitdinger et al. | |
| 5,700,247 A | 12/1997 | Grimard et al. | |
| 5,851,197 A | 12/1998 | Marano et al. | |
| 5,876,379 A | 3/1999 | Beauvais et al. | |
| 6,093,172 A | 7/2000 | Funderburk et al. | |
| 6,210,369 B1 | 4/2001 | Wilmot et al. | |
| 6,293,925 B1 | 9/2001 | Safabash et al. | |
| 6,607,509 B2 | 8/2003 | Bobroff et al. | |
| 6,997,907 B2 | 2/2006 | Safabash et al. | |
| 7,207,974 B2 | 4/2007 | Safabash et al. | |
| 7,318,816 B2 | 1/2008 | Bobroff et al. | |
| 7,329,239 B2 | 2/2008 | Safabash et al. | |
| 8,292,849 B2 | 10/2012 | Bobroff et al. | |
| 8,628,498 B2 | 1/2014 | Safabash et al. | |
| 8,641,674 B2 | 2/2014 | Bobroff et al. | |
| 8,672,881 B2* | 3/2014 | Nagamatsu ....... A61M 25/1002 604/97.02 | |
| 9,138,343 B2 | 9/2015 | Stout et al. | |
| 9,220,631 B2 | 12/2015 | Sigg et al. | |
| 9,421,129 B2 | 8/2016 | Lerner | |
| 9,504,603 B2 | 11/2016 | Lerner | |
| 9,603,739 B2 | 3/2017 | Lerner | |
| 9,889,248 B2* | 2/2018 | Head ..................... A61M 5/002 | |
| 9,895,259 B2 | 2/2018 | Lerner | |
| 9,913,750 B2 | 3/2018 | Lerner | |
| 10,478,335 B2 | 11/2019 | Lerner | |
| 10,524,957 B2 | 1/2020 | Lerner | |
| D906,102 S | 12/2020 | Cook et al. | |
| D934,069 S | 10/2021 | Cook et al. | |
| 11,160,918 B2 | 11/2021 | Cook et al. | |
| 11,793,926 B2 | 10/2023 | Cook et al. | |
| 2002/0022855 A1 | 2/2002 | Bobroff et al. | |
| 2002/0198499 A1 | 12/2002 | Hu | |
| 2003/0125669 A1 | 7/2003 | Safabash et al. | |
| 2003/0130619 A1 | 7/2003 | Safabash et al. | |
| 2003/0158520 A1 | 8/2003 | Safabash et al. | |
| 2003/0199823 A1 | 10/2003 | Bobroff et al. | |
| 2004/0002682 A1 | 1/2004 | Kovelman et al. | |
| 2006/0161114 A1 | 7/2006 | Perot et al. | |
| 2010/0016807 A1 | 1/2010 | Thilly | |
| 2011/0040256 A1 | 2/2011 | Bobroff et al. | |
| 2011/0190709 A1 | 8/2011 | Mitsuno et al. | |
| 2011/0257597 A1 | 10/2011 | Safabash et al. | |
| 2012/0041388 A1* | 2/2012 | Blomquist ............... A61D 7/00 604/227 |
| 2012/0109072 A1 | 5/2012 | Tabata et al. | |
| 2012/0310046 A1 | 12/2012 | Stout et al. | |
| 2012/0310215 A1 | 12/2012 | Stout et al. | |
| 2013/0018317 A1 | 1/2013 | Bobroff et al. | |
| 2013/0053788 A1* | 2/2013 | Dugand ............... A61M 5/3245 604/198 |
| 2013/0296825 A1 | 11/2013 | Lerner | |
| 2014/0012227 A1* | 1/2014 | Sigg ..................... A61K 9/0048 604/506 |
| 2014/0039456 A1 | 2/2014 | Lerner | |
| 2014/0094756 A1 | 4/2014 | Bobroff et al. | |
| 2014/0107581 A1 | 4/2014 | Safabash et al. | |
| 2015/0105734 A1 | 4/2015 | Bryant et al. | |
| 2015/0366584 A1 | 12/2015 | Stout et al. | |
| 2015/0366708 A1 | 12/2015 | Lerner | |
| 2017/0100284 A1 | 4/2017 | Lerner | |
| 2017/0165113 A1 | 6/2017 | Lerner | |
| 2017/0172795 A1 | 6/2017 | Lerner | |
| 2018/0117256 A1* | 5/2018 | Ruddocks ............. A61F 9/0017 |
| 2018/0228649 A1 | 8/2018 | Lerner | |
| 2018/0250474 A1 | 9/2018 | Wei | |
| 2018/0263816 A1 | 9/2018 | Lerner | |
| 2018/0326126 A1 | 11/2018 | Fiedler | |
| 2018/0333300 A1 | 11/2018 | Lerner | |
| 2018/0344523 A1 | 12/2018 | Lerner | |
| 2018/0360656 A1 | 12/2018 | Lerner | |
| 2019/0290857 A1 | 9/2019 | Ferraro | |
| 2019/0365565 A1 | 12/2019 | Bryant et al. | |
| 2021/0008284 A1 | 1/2021 | Fiedler | |
| 2022/0362441 A1 | 11/2022 | Fiedler | |
| 2023/0080971 A1 | 3/2023 | Miller | |
| 2023/0248898 A1 | 8/2023 | Cook et al. | |

FOREIGN PATENT DOCUMENTS

| | | |
|---|---|---|
| TW | 201707738 A | 3/2017 |
| WO | WO-1997044076 A1 | 11/1997 |
| WO | WO-1998033549 A1 | 8/1998 |
| WO | WO-1999030759 A2 | 6/1999 |
| WO | WO-1999033504 A1 | 7/1999 |
| WO | WO-2002100457 A2 | 12/2002 |
| WO | WO-2007116086 A1 | 10/2007 |
| WO | WO-2008116908 A1 | 10/2008 |
| WO | WO-2009154107 A1 | 12/2009 |
| WO | WO-2010024209 A1 | 3/2010 |
| WO | WO-2011/122351 A1 | 10/2011 |
| WO | WO-2012166799 A2 | 12/2012 |
| WO | WO-2012166805 A1 | 12/2012 |
| WO | WO-2013/028537 A2 | 2/2013 |
| WO | WO-2013151904 A1 | 10/2013 |
| WO | WO-2013178771 A1 | 12/2013 |
| WO | WO-2014005728 A1 | 1/2014 |
| WO | WO-2014/187779 A1 | 11/2014 |
| WO | WO-2015054075 A1 | 4/2015 |
| WO | WO-2018215580 A1 | 11/2018 |
| WO | WO-2019149869 A2 | 8/2019 |
| WO | WO-2019183057 A1 | 9/2019 |

OTHER PUBLICATIONS

Office Action received in counterpart Taiwanese Patent Application No. 109130012, dated Feb. 15, 2024.

* cited by examiner

INJECTION DEVICE FOR DRUG DELIVERY AND PACKAGING FOR THE INJECTION DEVICE

CROSS-REFERENCE TO RELATED APPLICATION

Priority is claimed to U.S. Provisional Patent Application No. 62/895,456, filed Sep. 3, 2019, and U.S. Provisional Patent Application No. 63/018,141, filed Apr. 30, 2020, the entire contents of each of which is hereby incorporated by reference.

FIELD OF THE INVENTION

This disclosure generally relates to injection device for drug delivery and packaging for the injection device. More particularly, the disclosure generally relates to a backstop for the injection device which improves grip, usability, and or ergonomic design of the injection device and/or reduces or prevents inadvertent movement of a plunger rod and/or a stopper component associated with the injection device and packaging for identifying, securing, and/or holding the injection device.

BACKGROUND

As is known in the art, syringes are medical delivery devices used to administer a medicament to a patient. Syringes are often marketed either in prefilled form, wherein a set dosage of medicament is already provided therein, or they are empty and intended to be filled from a vial or other source of medicament by an end user at the time administration of the medicament is desired.

Syringes often include a barrel portion adapted to retain the medicament. The distal end of the barrel is often configured to include and/or mate with a conventional piercing element, such as a pointed needle cannula or a blunt ended cannula, to deliver the medicament contained in the barrel. The piercing element may be made of steel, plastic, or any other suitable material. A plunger rod may be inserted through the open proximal end of the syringe barrel and, through its engagement with an elastomeric or rubber-like stopper element fitted in a substantially fluid-tight manner within the interior of the barrel, a user can apply manual force to the plunger to deliver the medicament through the piercing element. A flange is also often provided around the open distal end of the syringe barrel as a form of finger rest to facilitate a user's manipulation of the device. The syringe may also include backstop or component (a.k.a. "a backstop") that is coupled with or connected to the flange to improve grip, usability, and or ergonomic design of the syringe. As a more specific example, the backstop may have a radial length that is greater than the length of the flange, thereby effectively extending the length of the grip surface. The backstop and/or the plunger rod may also or alternatively reduce or prevent inadvertent movement of the plunger rod and/or a stopper component. As a more specific example, backstop and/or the plunger rod may have component(s) that engage with each other to define a maximum point, in the retraction direction, that the plunger rod may be moved.

It may be desirable, both for integrity of the medicament as well as for patient safety, to sufficiently sterilize the components of the syringe. Sterilization may occur at several stages in the assembly process, including pre-fill stages (e.g., sterilization of the empty barrel and/or plunger) and post-fill stages (e.g., external sterilization of the assembled pre-filled syringe). External sterilization typically occurs after the pre-filled syringe has been filled, fully assembled, and located in at least some portion(s) of its final packaging. For some indications of use, such as certain ophthalmic indications, federal regulations may require external sterilization under certain conditions, parameters, and/or results.

External sterilization may pose design challenges. For example, medicament may be sensitive to sterilization and/ or conditions thereof, such as temperatures, gases, radiation. Additionally, particularly in view of sensitivities of the medicament, it may be difficult to achieve a desired or required level of sterilization for the syringe and/or components thereof. As a more specific example, surface interactions between various components of the syringe and/or the packaging may create or promote occluded spaces that may not be sterilized effectively and/or completely during external sterilization steps performed on the syringe. As a more specific example, surface interactions between the syringe and the backstop and/or the syringe and the packaging may create or promote occluded spaces. If occluded spaces prevent or resist an effective level of sterilant gas from reaching an area, then that are may not be effectively sterilized. If occluded spaces prevent or resist which prevent sterilant gas from being purged from an area, a patient could develop a superficial eye infection or a more serious condition such as endophthalmitis, such as patients that are already visually compromised before treatment. Therefore, it is desirable to maintain integrity of the medicament while reaching a suitable level of sterilization for all relevant portions and components of the syringe.

The present disclosure sets forth injection devices embodying advantageous alternatives to existing injection devices and packaging for the same, and that may address one or more of the challenges or needs mentioned herein, as well as provide other benefits and advantages.

SUMMARY

An injection device is provided, including a syringe having a barrel and a flange and a backstop configured to be coupled with the syringe adjacent to the flange. The backstop may have an inner surface generally extending around at least a portion of the syringe, wherein the inner surface includes at least one protrusion extending away from the inner surface and configured to engage the flange and/or the barrel to permit or promote airflow through a space between the inner surface and the syringe.

The injection device may include at least two protrusions extending away from the inner surface and configured to engage the flange and/or the barrel to permit or promote airflow through the space between the inner surface and the syringe. It may also include another number of protrusions, such as three, four, five, six, seven, or another suitable number.

The injection device may include a collar portion defining the inner surface generally extending around at least a portion of the barrel. It may also or alternatively be configured to engage the syringe in a snap-fit relationship.

The at least one protrusion may be a rib extending generally parallel with the axis of the syringe.

The backstop may define a cavity for receiving at least a portion of the flange. The cavity may include opposing surfaces defining the cavity and the at least one protrusion may extend away from at least one of the opposing surfaces. The at least one protrusion may include at least one protrusion on a top opposing surface and at least one protrusion on a bottom opposing surface. Additionally or alternatively, the at least one protrusion may include at least two ribs on the top opposing surface and at least two ribs on the bottom opposing surface.

The injection device may be a pre-filled syringe containing a medicament, such as a VEGF antagonist. For example, the VEGF antagonist may be a non-antibody VEGF antagonist. As another example, the non-antibody VEGF antagonist can be a VEGF-Trap. The VEGF-Trap may be an aflibercept.

The injection device may also or alternatively include a packaging configured to receive and/or support the syringe, wherein the packaging includes a cavity surface and at least one protrusion extending away from the cavity surface, the at least one protrusion configured to engage the barrel of the syringe to permit or promote airflow through a space between the cavity surface and the syringe.

The injection device may also or alternatively include a packaging configured to receive and/or support the syringe, wherein the packaging includes a cavity surface defining at least one stop surface configured to engage the barrel of the syringe and resist and/or limit movement of the plunger rod.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally relates to injection devices which can be safely and reliably activated by a user for administering a drug, or in the case where a patient is the user, self-administering a drug. More particularly, the disclosure generally relates to an injection device including a syringe and a backstop and/or packaging configured to receive and/or support the syringe. The injection device may be a syringe, such as a pre-filled syringe containing a medicament. These components, whether separate or together, may be suitable for external sterilization steps. As a more specific example, utilizing these components separate or together may allow a manufacturer or user to utilize a desired bioburden kill level while minimizing or avoiding undesirable effects on the medicament.

The term "about" as used herein means +/−10% to the smallest significant digit.

Figure 13A:
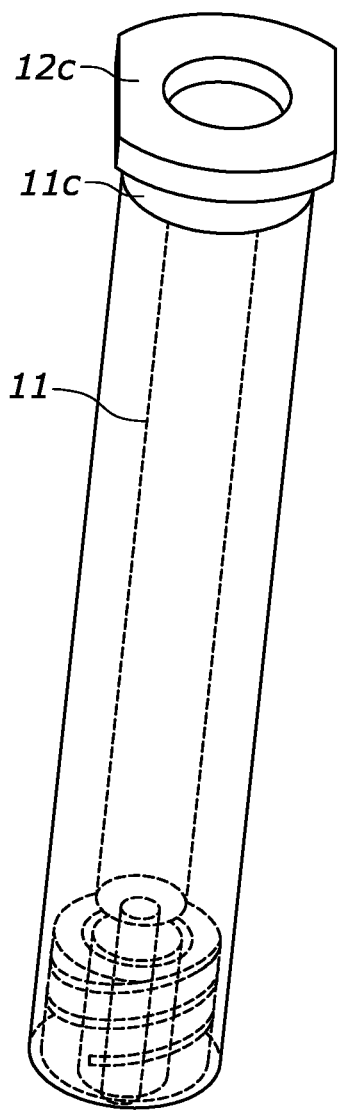
FIGS. 13A-13C show various perspective views of the syringe from FIG. 1, highlighting areas of the syringe that may be particularly susceptible to gas occlusion during and after an external sterilization process.
Figure 13B:
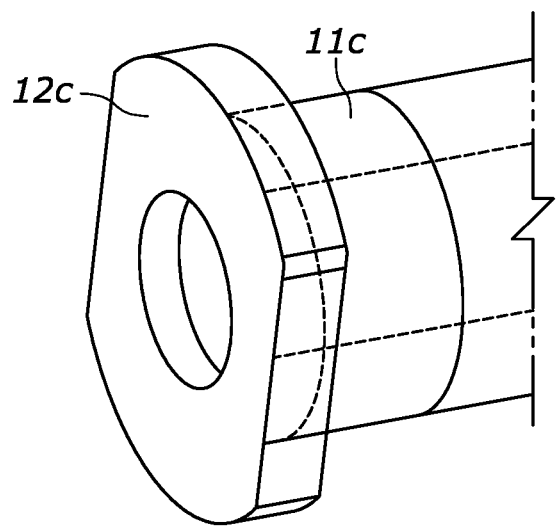
Figure 13C:
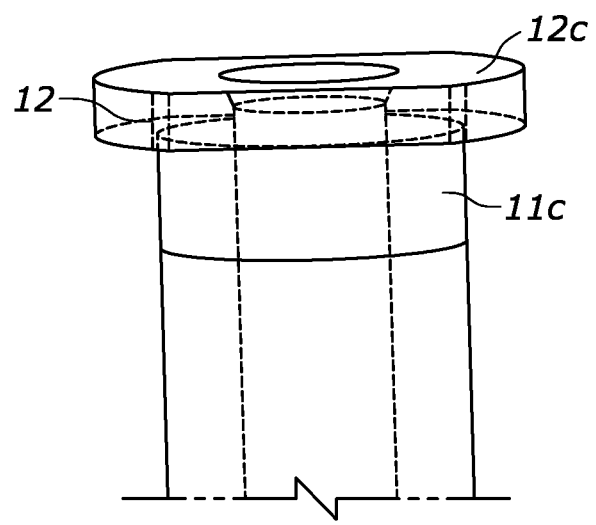

Due to the engagement between backstops and syringes known in the art, sterilization gas may fail to reach occluded or partially occluded spaces between respective backstop and syringes and thereby fail to fully or suitably sterilize those surfaces. Additionally, or alternatively, the sterilization gas may not be effectively purged from these occluded or partially occluded spaces, thereby exposing the drug to the sterilization gas beyond the specified sterilization step in the chamber. Either and/or both of these situations may be undesirable. As a more specific example, FIGS. 13A-13C include various views of a syringe barrel and flange, with surfaces of the same that may be particularly susceptible to occlusion shown with dark shading and identified with numeral 11c (a proximal section of the barrel 11) and numeral 12c (a proximal section of the flange 12). For example, a flange upper surface 12c and a barrel outer surface 11c may be particularly susceptible to occlusion due to their respective engagements with backstops known in the art.

Figure 1:
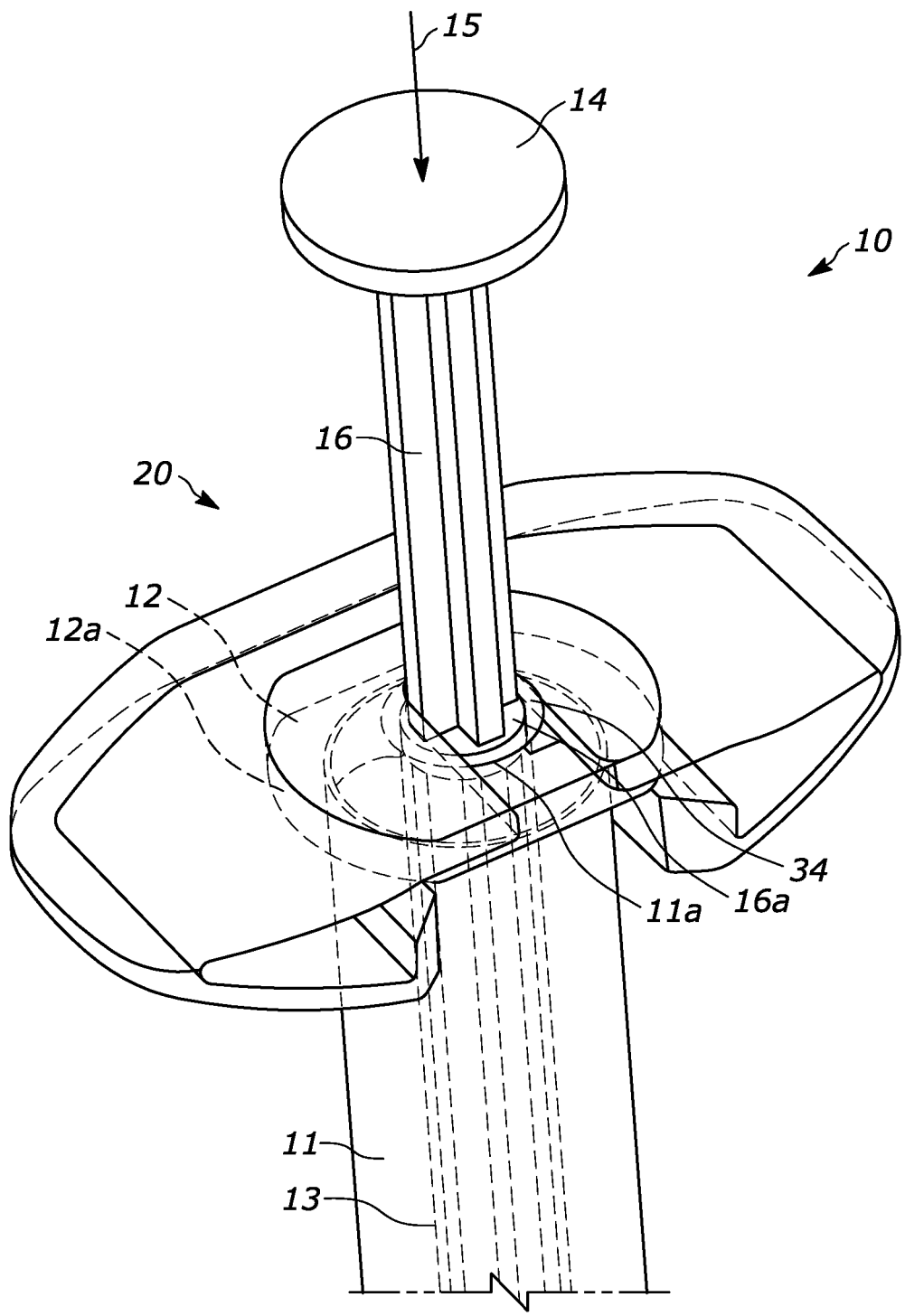
FIG. 1 is a perspective view of an exemplary injection device according to aspects of the present disclosure, and having a syringe, having a barrel (partially shown), a flange, a plunger rod (partially shown), and a backstop.

FIG. 1 is a perspective view of an injection device 10, such as a syringe 10 generally having a barrel 11 having a proximal open end 11a, a distal end 11b (FIGS. 2A, 2B, 12A and 12B), a cavity 13, a flange portion 12, a plunger rod 16, a stopper component 18 (FIGS. 12A and 12B), and a backstop 20.

The syringe barrel distal end 11b includes and/or supports a needle or other suitable component for completing a fluid path into the patient. For example, the syringe barrel distal end may include a Luer lock component 17 (FIGS. 2A and 2B) and/or a protective cap 19 (FIG. 12A) covering the same. Before use the protective cap 19 may be removed so the Luer lock component 17 may receive a needle. The syringe barrel proximal end 11a (see FIG. 2A) may receive the plunger rod 16 for pushing the stopper component 18 in the distal direction 15 and ejecting the drug from the syringe 10. For example, the stopper component 18 may form a fluid-tight relationship with the cavity 13 while also able to travel in the distal direction 15 along the cavity 13 and urge the drug from the distal end of the syringe 10. The plunger rod 16 may include a plunger rod end 14 with a larger diameter than the body portion of the plunger rod 16 to limit the travel distance of the plunger rod 16 in the distal direction 15 and/or to make it easier for the user to depress the plunger rod 16. The plunger rod 16 may be a one-way component, such that the plunger rod is not fixedly connected to the stopper so that if the plunger rod 16 is moved in the proximal direction (opposite the distal direction 15) then the stopper 18 does not move with the plunger rod 16.

Figure 12A:
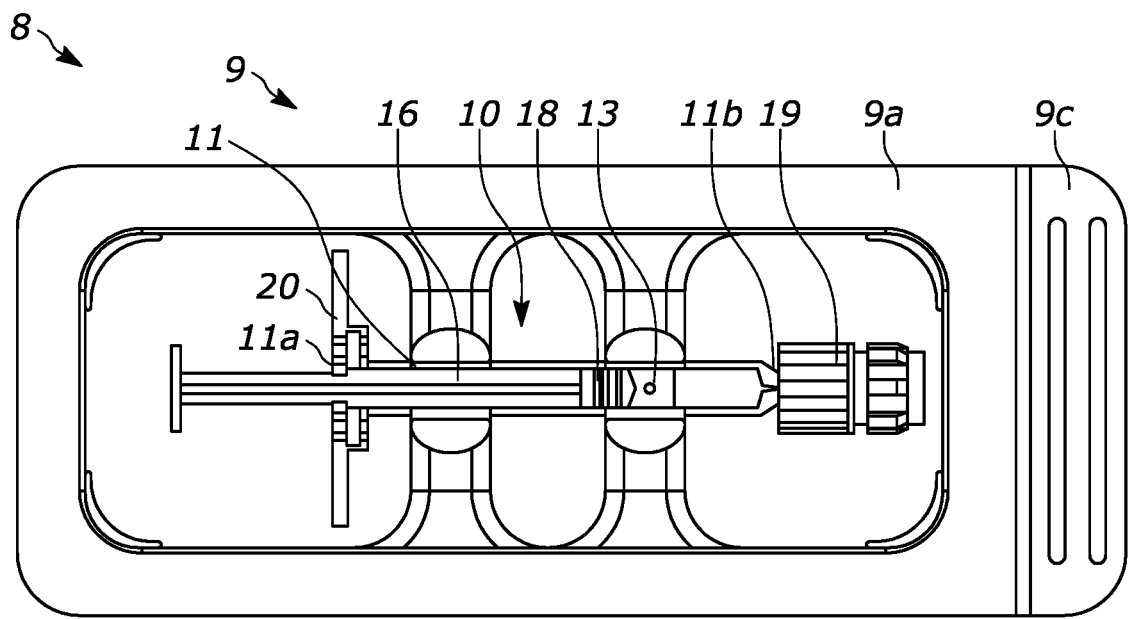
FIG. 12A is a top view of another exemplary packaging according to aspects of the present disclosure, with a top protective cover removed and which may be used for securing and/or holding an injection device, such as during external sterilization of the injection device.
Figure 12B:
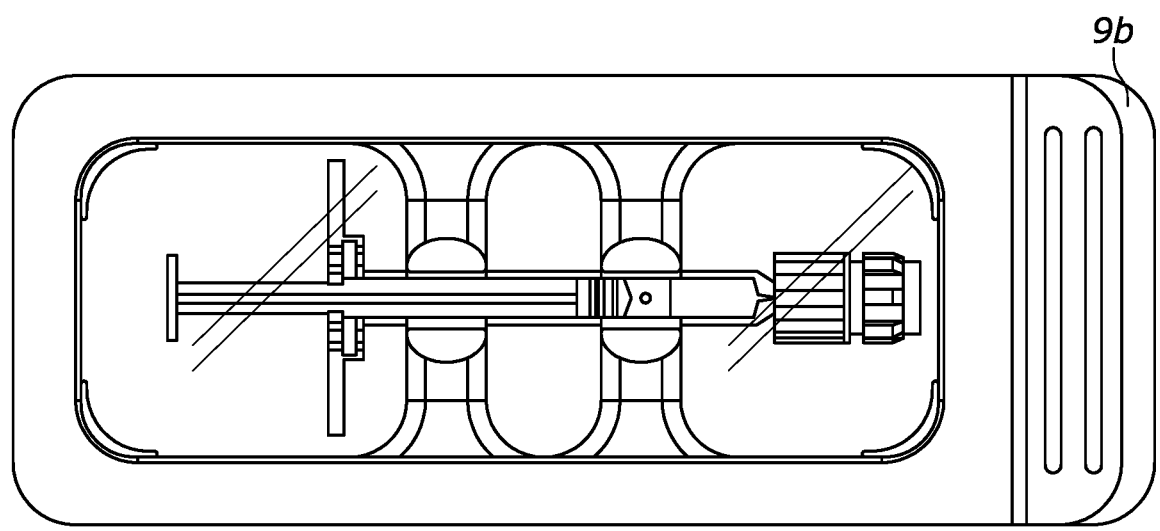
FIG. 12B is a top view of the exemplary packaging shown in FIG. 12A, with the top protective cover in-place.

FIGS. 12A and 12B show the syringe 10 positioned within a packaging 9 such as a blister pack 9 (collectively the packaged syringe 8). The packaging 9 includes a base portion 9a and a cover 9b (FIG. 12B) such as a Tyvek cover 9b that extends substantially or completely across the base portion 9a and/or is sealed thereto. The Tivek cover 9b may extend outside of the border of the base portion 9a in at least one portion, such as one side, to make it easier to remove the Tyvek cover 9b. Additionally or alternatively, the base portion 9a may include a tab portion 9c that is not sealed with the Tyvek cover 9b to promote easy removal.

The syringe barrel 11 may be made of plastic, glass, or any suitable material. As a more specific example, the syringe barrel may be made of a plastic material including at least one or more of the following materials: certain grades of polypropylene (homo-polymer and/or co-polymer polypropylene), cyclo-olefin copolymer, cyclo-olefin polymer, cyclic olefin copolymer (COC), cyclo olefin polymer (COP), or other suitable materials. As a more specific example, the syringe barrel may be made of cyclo olefin polymer (COP).

The backstop 20 may be coupled with or connected with the syringe 10 to improve grip, usability, and or ergonomic design of the syringe. The flange 12 may include a diameter larger than that of the syringe barrel 11 and may serve as a finger rest permitting the user to manipulate the syringe 10 during use. For example, the user may rest two or more of her/his fingers against the flange 12 while using her/his thumb to depress the plunger rod end 14. As a more specific example, the backstop 20 may be coupled with the flange portion 12 to effectively extend the flange portion and thereby extend the length of the grip surface. As an even more specific example, it may be desirable to for a user to have a larger effective grip surfaces to improve grip, usability, and or ergonomic design of the syringe, particularly for certain applications of the syringe such as ophthalmic indications. However, it may be undesirable to increase the size of the flange portion 12 due to space constraints during manufacturing and shipping, advantages of scale for using a standard syringe/flange configuration. Additionally, syringes are commonly used in autoinjectors, which have a profile that may not accommodate a syringe with an enlarged flange size. Therefore, it may be desirable to have an additional component, such as a backstop component, that is able to be attached to and/or coupled with the syringe at a point in the manufacturing process.

The backstop may be manufactured from any suitable material. For example, it may be molded out of polypropylene ("PP") or acrylonitrile butadiene styrene ("ABS"). ABS may have the advantage of being stiffer than PP and other materials so that the backstop can become lighter. As a more specific example, if the backstop is made from PP it may have a minimum wall thickness of 1.5 mm thickness, whereas if it is made from ABS it may have a minimum wall thickness of 1 mm.

The backstop 20 may also be utilized to limit, restrict, reduce, or prevent inadvertent movement of the stopper component 18 with respect to the syringe 10. For example, the backstop 20 may fit over the flange 12 to reduce or prevent inadvertent movement of a plunger rod 16. For example, as shown in FIG. 1, the backstop 20 may have locking surface 34 that engages the plunger rod 16 and restricts or prevents relative motion between the two components in the distal direction 15. As a more specific example, the plunger rod 16 may have a lock ring 16a that has a larger diameter than the rest of the plunger rod 16 but a smaller diameter than the cavity; and the backstop 20 locking surface 34 may have a smaller diameter than the lock ring 16*a* so that the lock ring 16*a* is unable to travel in the proximal direction past the backstop 20. This arrangement would act to limit the proximal direction movement of the plunger rod 16.

For the above-discussed reasons, and perhaps others, the user typically does not remove the backstop 20 before using the syringe 10.

It may be desirable and/or required by regulations to externally sterilize an injection device during the manufacturing and/or assembly process. Additionally, some applications for pre-filled syringes (such as certain ophthalmic applications) require external sterilization. For example, 21 CFR 200.50 indicates, "Ophthalmic preparations and dispensers should be sterile." Furthermore, ANSI/AAMI ST67: 2011/(R)2017 states, "Sterilization of health care products—Requirements and guidance for selecting a sterility assurance level (SAL) for products labeled 'sterile" and Section 4.1.1—states: "Generally an SAL value of 10-6 has been used for terminal sterilization of health care products." Furthermore, Annex A to the ST67 and EN556-1:2006 provide: "Sterilization of medical devices—Requirements for medical devices to be designated "STERILE"—Part 1: Requirements for terminally sterilized medical devices" . . . Section 4.1: "For a terminally-sterilized medical device to be designated "STERILE", the theoretical probability of therebeing a viable micro-organism present on/in the device shall be equal to or less than 1×10–6." Therefore, it may be desirable and/or required for a bioburden to be less than 1×10–6 (e.g., $1 \times 10^{-6}$).

Therefore, the disclosed embodiments herein are particularly advantageous for these types of applications. The terms "external sterilization" and/or "externally sterilize" as used herein refer to the process of sterilizing an injection device after it has been assembled. For example, the injection device shown in the figures may be externally sterilized after the syringe 10 (with a drug in the cavity 13), plunger rod 16, backstop 20, and protective cap (not shown) have all been assembled. During the external sterilization process, the injection device is typically placed in a sterilization chamber and exposed to a sterilization gas, such as Ethylene Oxide (EtO), Nitrogen Dioxide (NO2), Vaporized Hydrogen Peroxide (VPHP), Carbon Dioxide (CO2), chlorine dioxide, or any other suitable gas, for a predetermined length of time and other specified conditions (such as temperature and pressure). Then, after the sterilization cycle, the sterilization gas is purged from the chamber and the injection device remains in the chamber (which is substantially or completely free of sterilization gas) for another predetermined length of time and other specified conditions (such as temperature and pressure).

Figure 2A:
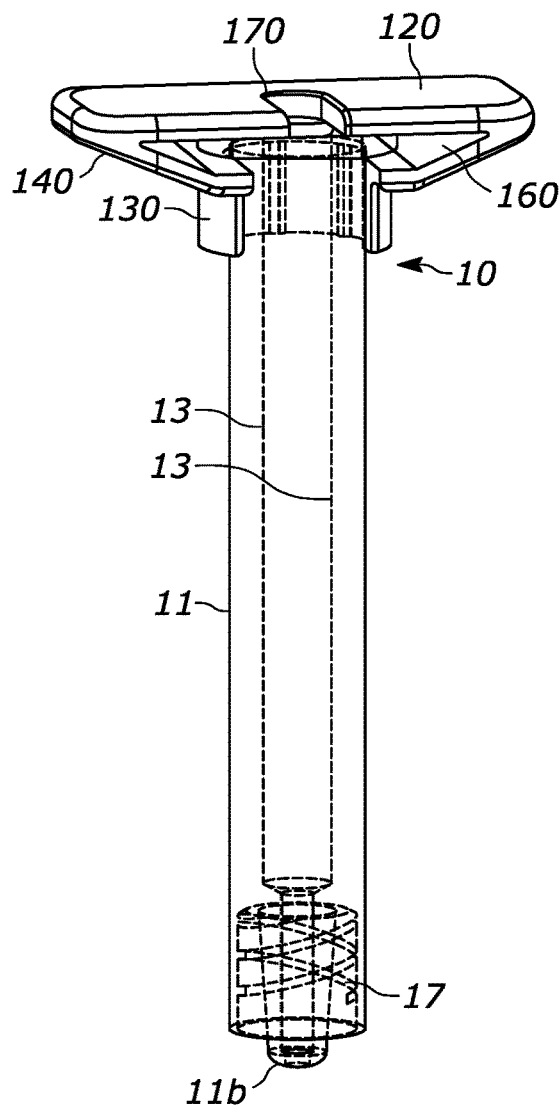
FIG. 2A is a perspective view of another exemplary injection device according to aspects of the present disclosure, and having a barrel, a flange, and a backstop.
Figure 2B:
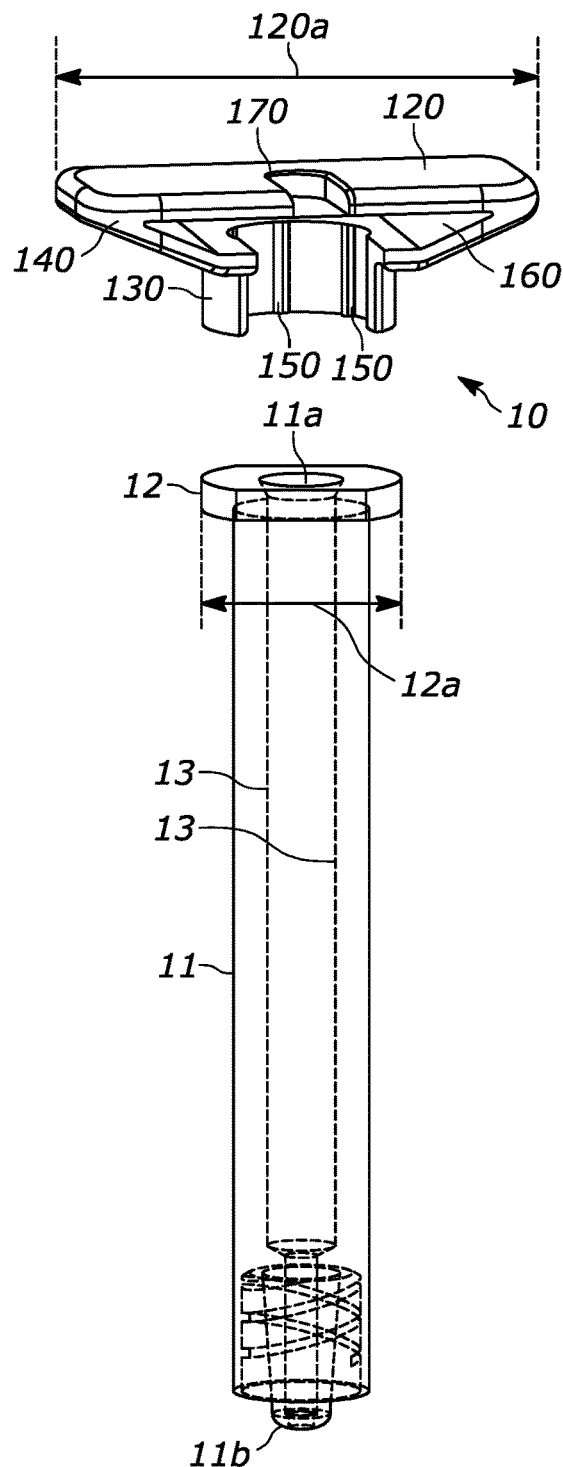
FIG. 2B is an exploded perspective view of the device shown in FIG. 2A showing the backstop decoupled from the barrel and flange.
Figure 2C:
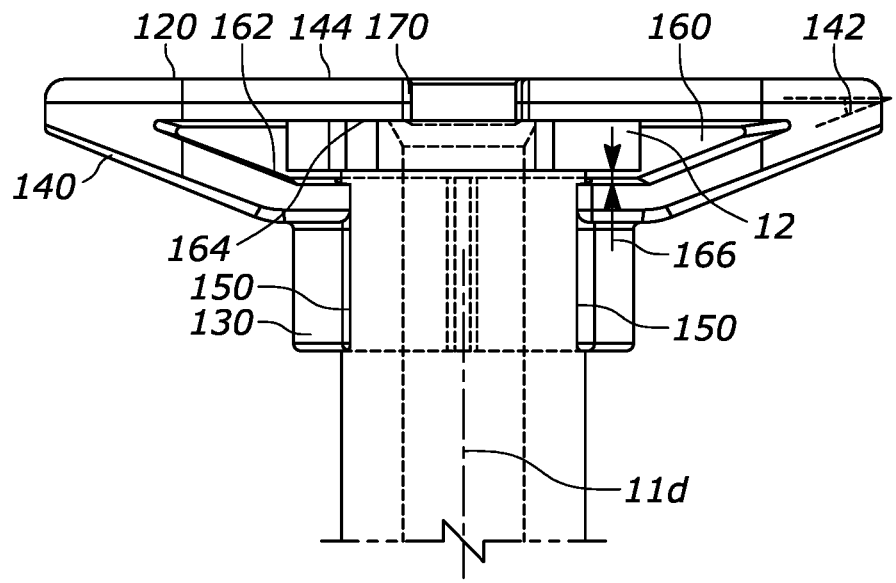
FIG. 2C is a front view of the device shown in FIG. 2A, showing the barrel (partial view) and the backstop.

FIGS. 2A through 2H, show another exemplary backstop 120, which may be utilized with a syringe 10 as shown in FIGS. 2A through 2C. The backstop 120 may generally include a collar portion 130 that extends around at least a portion of the syringe 10, an outer grip portion 140 for handling and/or gripping by the user, at least one protrusion such as a ridge 150 that helps permit or promote airflow through a space between the backstop and the syringe, a cavity 160 for receiving at least a portion of the syringe flange 12, and an opening 170 that permits the plunger rod 16 to extend through the backstop 120.

Figure 2D:
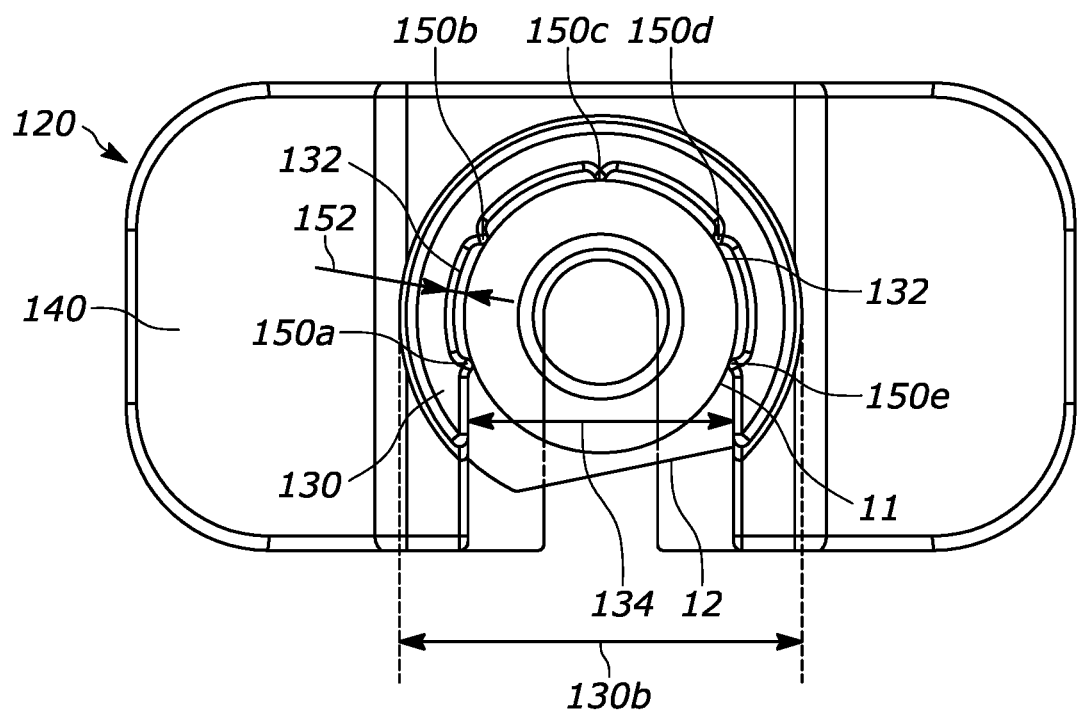
FIG. 2D is a bottom view of the backstop and the syringe shown in FIG. 2A.

The collar portion 130, as best shown in FIGS. 2D through 2H, defines an inner surface 132 that extends around at least a portion of the syringe 10. As a more specific example, the inner surface 132 is a generally annular surface that extends around a substantial portion of a circumference of the barrel 11 of the syringe 10. As an even more specific example, the inner surface 132 extends around a substantial portion of a circumference of the distal portion 11*c* of the barrel 11, the portion highlighted in FIGS. 13A-13C. In some versions, the "portion" of the circumference of the barrel 11 that is surrounded by the inner surface 132 can be a segment of the circumference of an area of the barrel 11, the entire circumference of an area of the barrel 11, or any other discrete area of a surface of the barrel 11. The inner surface 132 may have generally the same curvature as the barrel 11 and may extend around the barrel 11 for the length of the inner surface 132. As shown in FIG. 2D, the inner surface 132 may extend around the inner surface of the collar 130 in a generally circular/annular manner except where the collar 130 and inner surface 132 are interrupted across an opening 134 in the collar 130 that permits the backstop 120 to be coupled with the syringe 10. As a more specific example, the opening 134 permits the backstop 120 to receive the syringe 10 by sliding the syringe 10 towards the backstop 120 (or vice versa) until the syringe 10 contacts the backstop 120 in a snap-fit configuration. As another example, the inner surface 132 extends for approximately 270 degrees around the circumference of the barrel 11. The axial length of the collar 130 (measured along the axis of the barrel 11) is approximately 5 millimeters, but may have other suitable lengths. As the axial length of the collar 130 is increased, the connection between the syringe 10 and the backstop 120 may become more secure. Also or alternatively, as the axial length of the collar 130 is increased, the center of gravity may move farther away from the axial length midpoint, thereby making it easier to orient the backstop 120 during manufacturing. As a more specific example, it may be desirable to assemble the syringes via automation and to utilize a "shaker" or a "feeder" receptacle such as a pan or a bowl to cause a plurality of backstop components in a shaking tray to become similarly oriented to streamline the manufacturing process. The feeder bowl may, for example, have a central receptacle with a spiral-path track along the sidewall of the receptacle that carries parts around the sidewall and up towards the top rim of the receptacle, where the parts can be fed to the assembly station. Often, a feeder bowl is more reliable and/or effective when the center of gravity of the components is at least a certain distance away from the axial length midpoint of the component, thereby causing all or substantially of the components to tip over towards the "heavy side" of the component. The center of gravity of the backstop 120 is designated by numeral 136 in FIG. 2F. Additionally, a feeder is often more reliable if the parts have some asymmetric features (at least along one or two of the axes) so the feeder has a track edge or pattern that can urge improperly oriented parts back into the bowl. In this case, the track edge or pattern feature serves as a gate; if the parts are in the right orientation then they will not interact with the feature but if they are in the wrong orientation then they will interact with the feature and fall back into the bowl.

As discussed above, the backstop 120 provides the user with a larger effective gripping surface than the flange 12 of the syringe 10. As a more specific example, the flange portion 12 shown in FIGS. 2A and 2B has a generally oval or oblong shaped configuration with a maximum width 12*a* of approximately 13 millimeters and a barrel 11 diameter of approximately 9.5 millimeters. Therefore, the flange portion 12 has an effective grip surface of approximately 2 millimeters on each side of the flange portion 12. In comparison, the backstop 120 has a maximum width 120a of approximately 34 millimeters and a collar width 130b (FIGS. 2D and 2H) of approximately 12 millimeters. Therefore, the outer grip portion 140 of the backstop 120 has an effective grip surface of approximately 11 millimeters on each side of the collar 130.

The outer grip portion 140 has an angle 142 (FIG. 2C) of approximately negative 25 degrees with respect to the top surface 144 of the backstop 120. Therefore, the outer grip portion 140 has an angle of 115 degrees with respect to the syringe axis 11d. It may be desirable for the angle of the outer grip portion 140 with respect to the syringe axis 11d to be closer to 90 degrees than 180 degrees (i.e., 135 degrees or less) to allow the user to have a sufficient grip on the outer grip portion 140. It may be more desirable to have a smaller angle of the outer grip portion 140 with respect to the syringe axis 11d, such as 125 degrees or less, or 120 degrees or less, or 115 degrees or less. The outer grip portion 140 may also include a non-slip or grip-enhancement feature such as ribs or a material with a relatively high coefficient of friction.

Figure 2E:
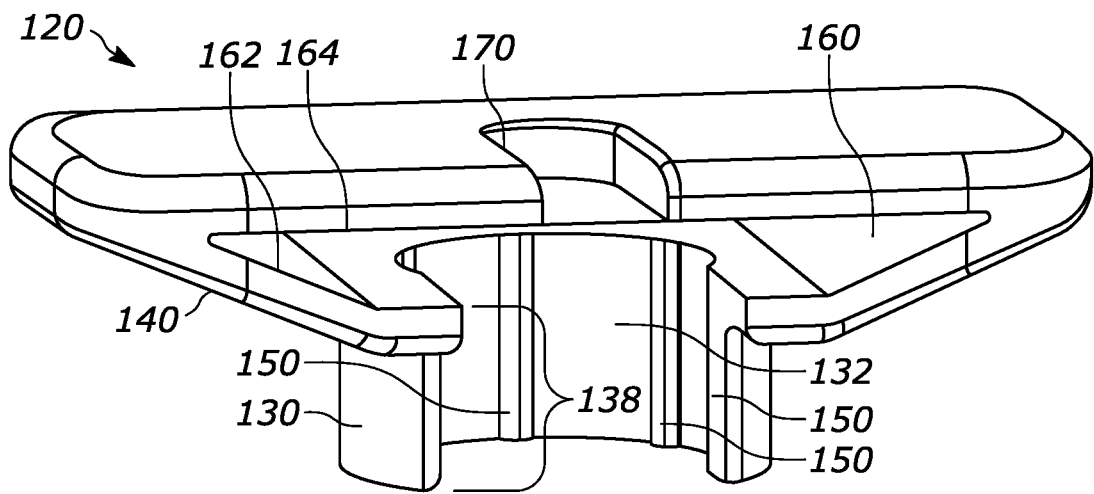
FIG. 2E is a perspective view of the backstop shown in FIG. 2B.

As discussed above, the backstop 120 may also include at least one protrusion such as at least one ridge 150 that engages the syringe 10 such that the collar inner surface 132 is spaced apart from the syringe 10. As a more specific example, the backstop inner surface 132 may include at least one protrusion 150 extending away from the inner surface 132 and configured to engage the flange 12 and/or the barrel 11 to permit or promote airflow through a space 152 between the inner surface 132 and the syringe 10. In FIGS. 2A through 2H, the backstop includes five ridges 150a, 150b, 150c, 150d, and 150e that are generally spaced apart from each other around the collar inner surface 132 and are more preferably generally equally spaced from each other so as to form a five-point engagement between the backstop 120 and the syringe 10. However, any suitable of ridges may be used, such as one, or two, or three, or four, or five, or six, or seven, or eight, or nine, or ten, or more. The ridges 150 may be integrally formed in the backstop 120 collar inner surface 132 or they may be separate components attached to the collar inner surface 132. In either case, the ridges 150 may cooperate to permit a relatively secure fit between the backstop 120 and the syringe 10 while creating the space 152 between the inner surface 132 and the syringe 10. For example, the ridges 150 may engage the barrel 11 in a snap-fit relationship. The ridges 150a, 150b, 150c, 150d, and 150e shown in the figures are generally parallel with the syringe axis 11d, but they may have an alternative configuration. The ridges 150a, 150b, 150c, 150d, and 150e shown in the figures may extend along the entire height 138 of the collar 130, as shown in FIG. 2E, or they may extend along only a portion of the height of the collar 130.

By permitting airflow through the space 152 (FIG. 2D) between the inner surface 132 and the syringe 10, the backstop 120 and the syringe 10 will cooperate to minimize or eliminate any occluded areas between the collar inner surface 132 and the barrel or the flange. For example, in one embodiment the ridges 150 are the only portions of the collar inner surface 132 that engage the barrel 11.

The protrusions on the backstop 120 shown in FIGS. 2A through 2H may instead have any suitable configuration that permits airflow the space 152 between the inner surface 132 and the syringe 10. For example, in one embodiment the protrusions may be replaced generally circular nodules, nubs, or other non-linear protrusion. As a more specific example, the protrusions on the backstop 120 may have a similar shape and size as the nodules shown in FIGS. 4A and 4B, but positioned on the collar 130 instead of within the cavity.

Figure 2F:
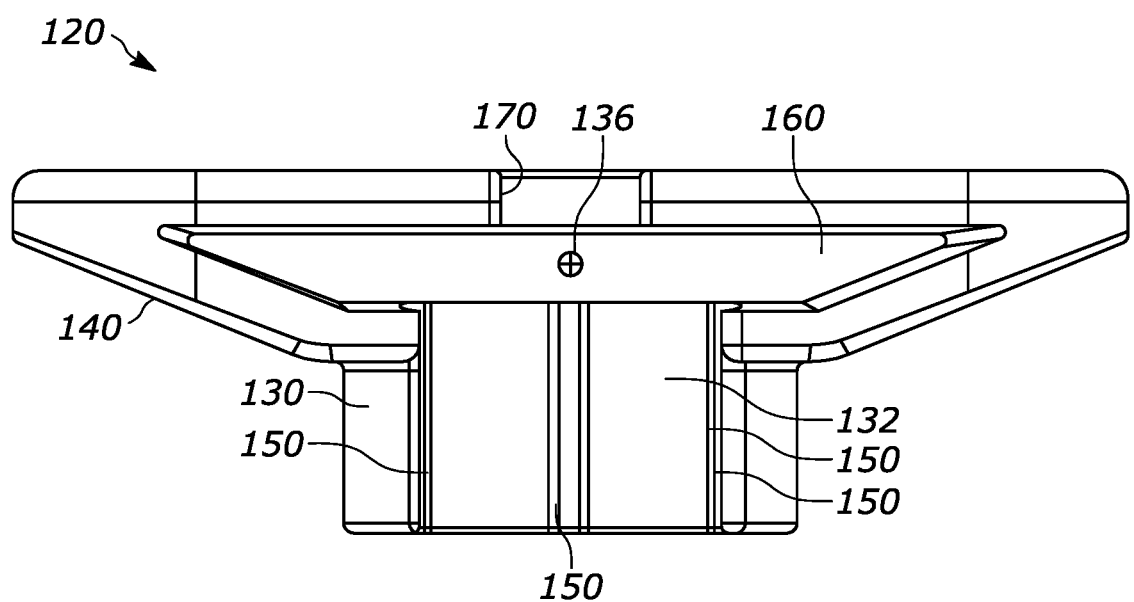
FIG. 2F is a front view of the backstop shown in FIG. 2B.
Figure 2G:
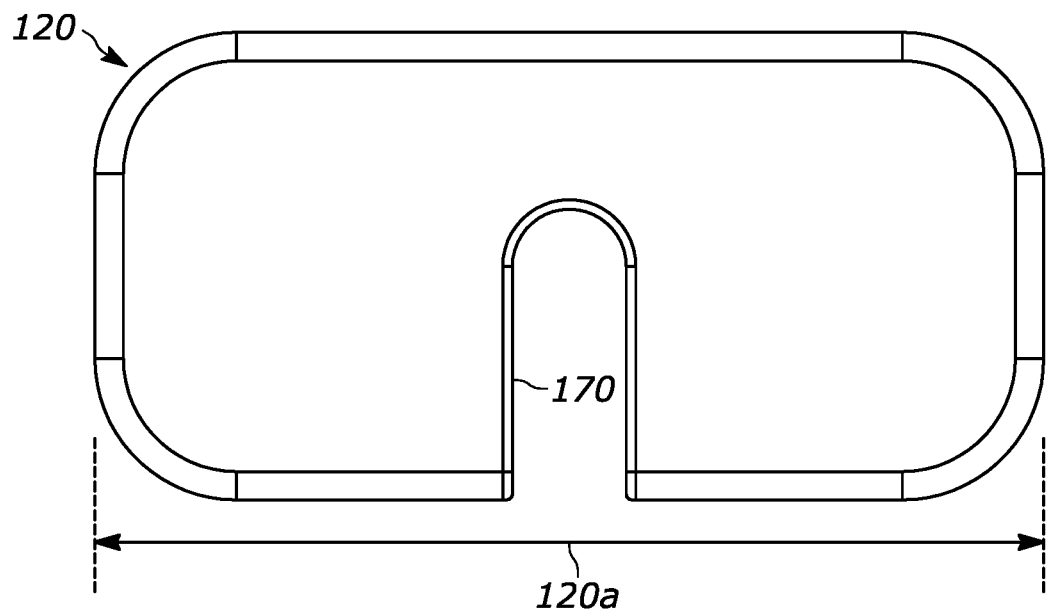
FIG. 2G is a top view of the backstop shown in FIG. 2B.
Figure 2H:
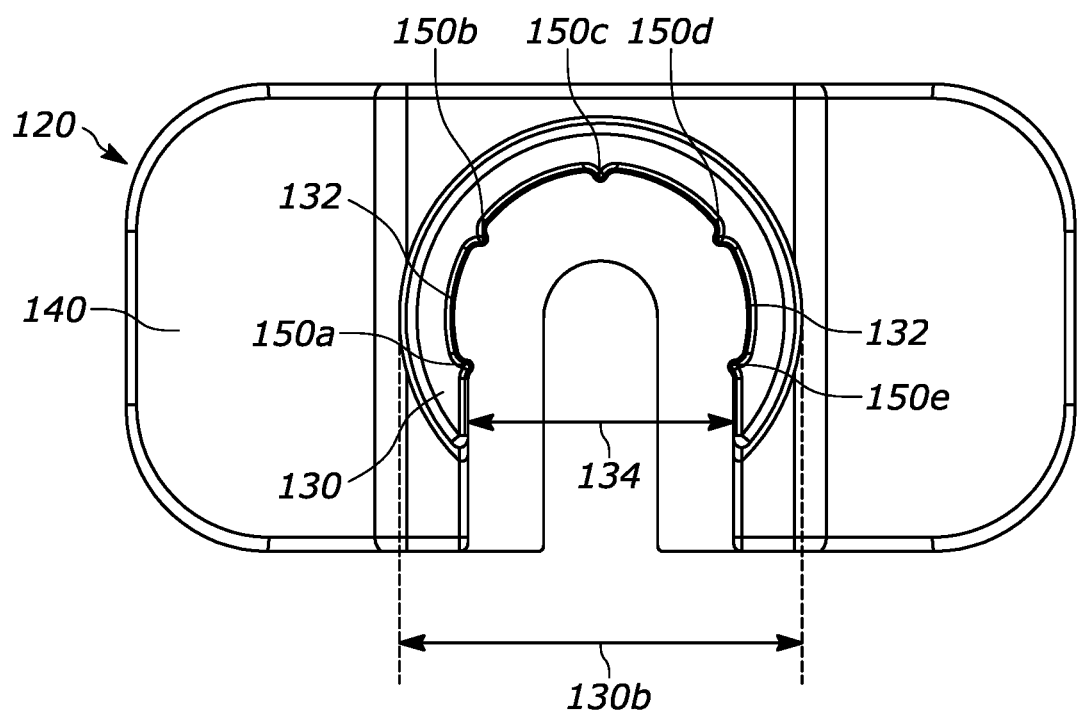
FIG. 2H is a bottom view of the backstop shown in FIG. 2B.

As introduced above, the backstop 120 includes the cavity 160 for receiving at least a portion of the syringe flange 12. As a more specific example, the cavity is defined by opposing surfaces 162, 164 (FIGS. 2E and 2F). As shown in FIG. 2C, the distance between the opposing surfaces 162, 164 may be larger than the axial height of the flange 12 such that a gap 166 exists between at least one of the opposing surfaces 162, 164 and the top and bottom surfaces of the flange 12. As a more specific example, the gap 166 shown in FIG. 2C is between the lower opposing surface 162 and the bottom surface of the flange 12, but in other configurations a similar gap may exist between the upper opposing surface 164 and the top surface of the flange or may exist on both sides (top and bottom) of the flange 12. The gap 166 and other similar gaps described herein may be advantageous for permitting or promoting airflow and/or preventing or reducing occluded space.

The cavity 160 is preferably shaped and sized to receive the entire flange 12 to promote a secure engagement between the collar 130 and the barrel 11. Also, the cavity 160 may be shaped and sized to receive the flange 12 in any orientation to simplify and/or improve manufacturing. For example, the cavity 160 may be shaped and sized to receive the flange 12 with its maximum width in any orientation. As a more specific example, the minimum width of the cavity 160 may be at least slightly larger than the maximum width of the flange 12 such that the flange can be inserted in any orientation and/or the flange 12 can freely rotate within the backstop 120.

As introduced above, the opening 170 permits the plunger rod 16 to extend through the backstop 120. The opening 170 may be sized to permit free movement of the plunger rod 16 except when the lock ring 16a abuts or engages the surface defining the opening 170. As a more specific example, the opening 170 may have a diameter or width that is at least slightly larger than the diameter or width of the portion of the plunger rod designated with numeral 16 in FIG. 1 (i.e., the section of the plunger rod with the plus-shaped cross-ssection) but the diameter or width of the opening 170 is at least slightly smaller than the diameter or width of the lock ring 16a, thereby preventing or restricting the plunger rod 16 from moving in the proximal direction past the point shown in FIG. 1.

Figure 3A:
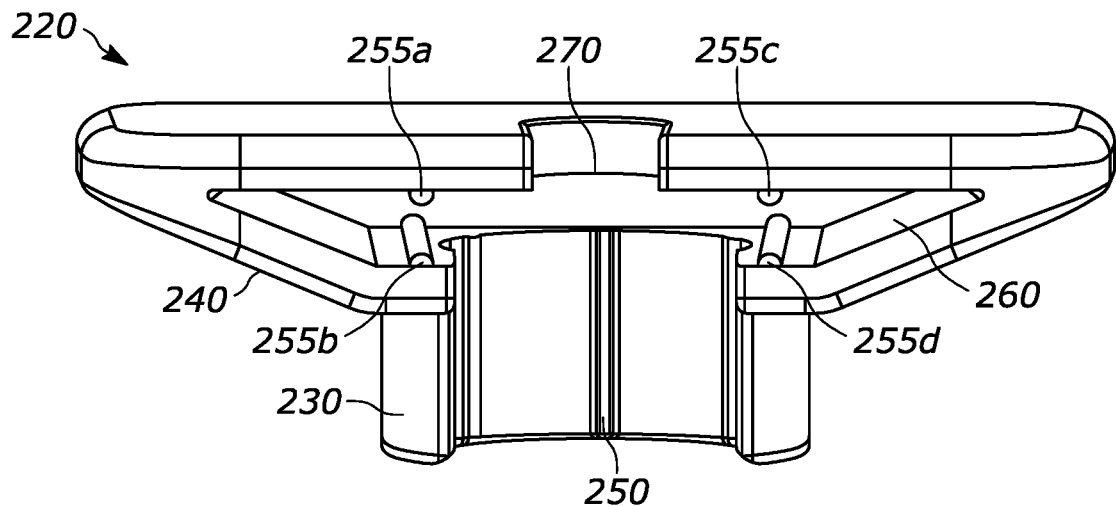
FIG. 3A is a perspective view, from above, of another exemplary backstop according to aspects of the present disclosure, and having a barrel, a flange, and a backstop.
Figure 3B:
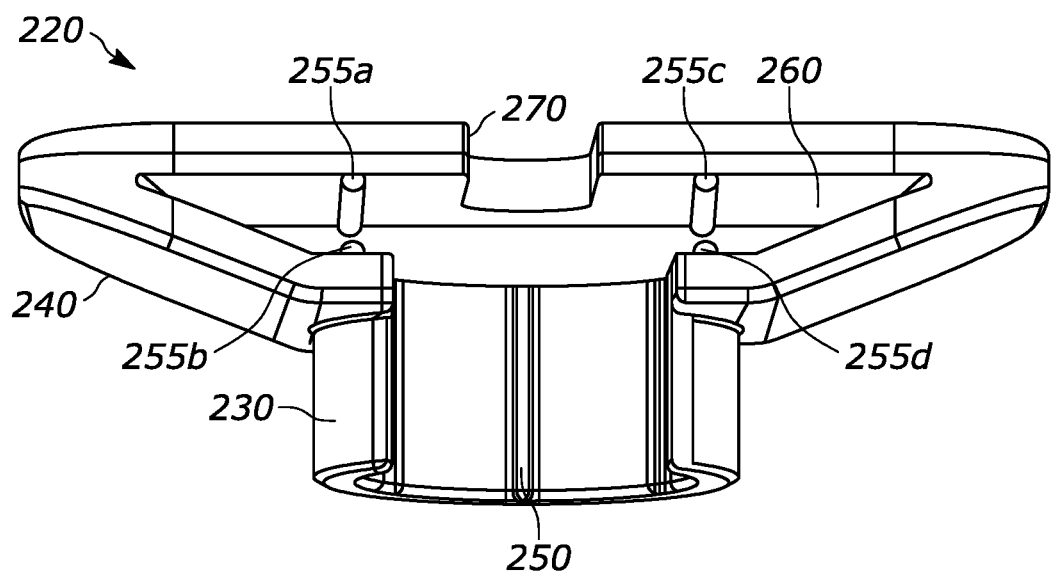
FIG. 3B is a perspective view, from below, of the backstop shown in FIG. 3A.

FIGS. 3A through 3B, show another exemplary backstop 220, which may be utilized with any suitable drug delivery device, for example a syringe such as syringe 10 shown in prior figures. The backstop 220 may generally include a collar portion 230 that extends around at least a portion of the syringe 10, an outer grip portion 240 for handling and/or gripping by the user, at least one protrusion such as a ridge 250 that helps permit or promote airflow through a space between the backstop and the syringe, a cavity 260 for receiving at least a portion of the syringe flange 12, and an opening 270 that permits the plunger rod 16 to extend through the backstop 220. The backstop 220 may include the features set forth in FIGS. 2A through 2H and the corresponding paragraphs describing the same, or other suitable features. Additionally, the backstop 220 further includes at least one protrusion 255 extending into the cavity 260. As a more specific example, the backstop 220 includes a plurality of ridges 255a, 255b, 255c, and 255d that each engage, abut, and/or are positioned adjacent to various portions of the flange 12 to permit or promote airflow within the cavity 260. This configuration may avoid or minimize a space or a gap between upper and lower opposing surfaces defining the cavity 260, thereby potentially providing a more secure connection between the syringe 10 and the backstop 220, while also minimizing or reducing occluded air spaces.

Figure 4A:
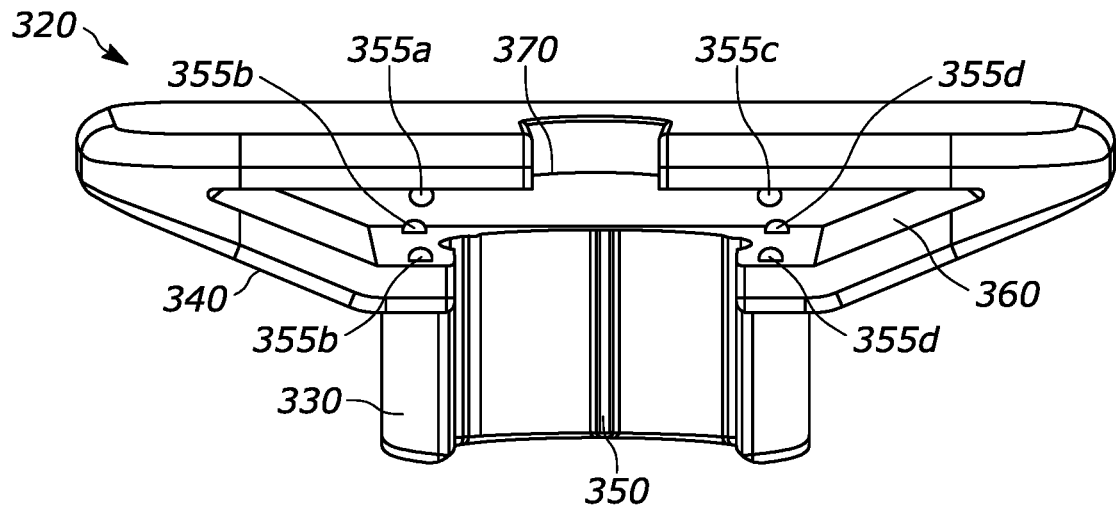
FIG. 4A is a perspective view, from above, of another exemplary backstop according to aspects of the present disclosure, and having a barrel, a flange, and a backstop.
Figure 4B:
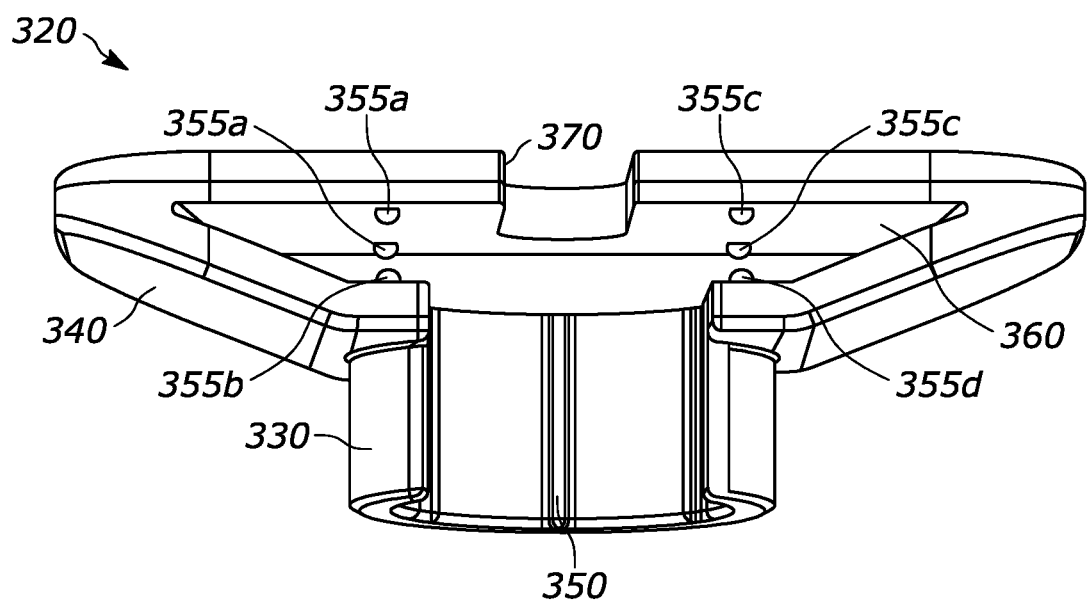
FIG. 4B is a perspective view, from below, of the backstop shown in FIG. 4A.
Figure 5A:
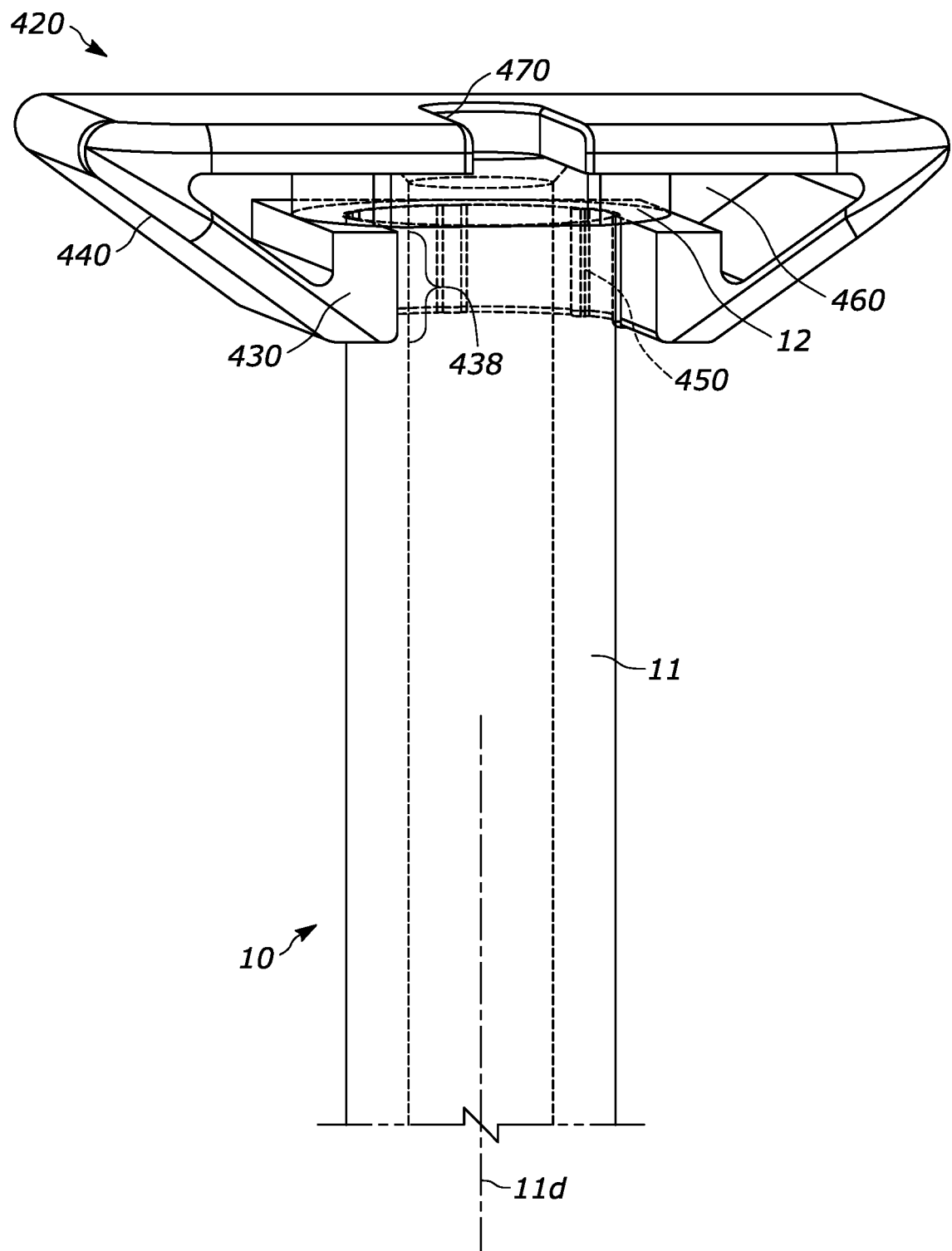
FIG. 5A is a perspective view of another exemplary injection device according to aspects of the present disclosure, and having a barrel (partially shown), a flange, and a backstop.
Figure 5B:
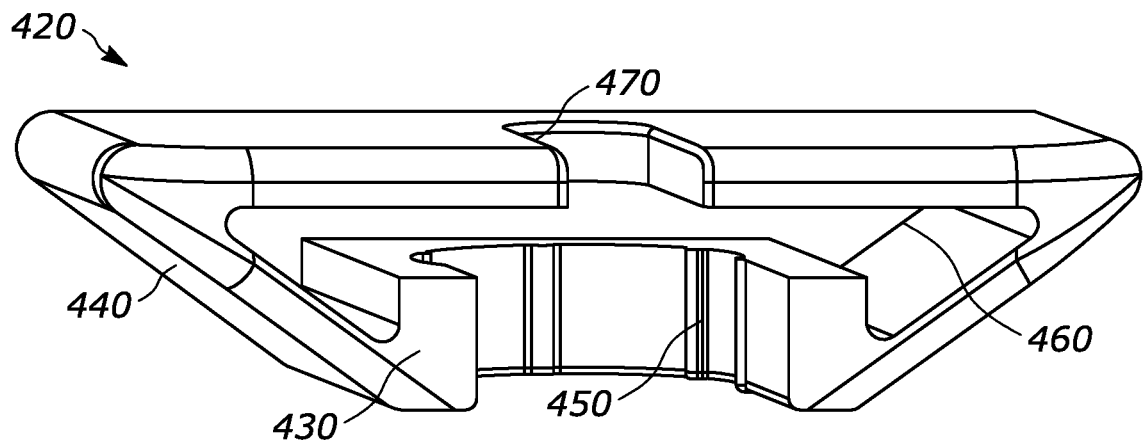
FIG. 5B is a perspective view of the backstop shown in FIG. 5A.
Figure 5C:
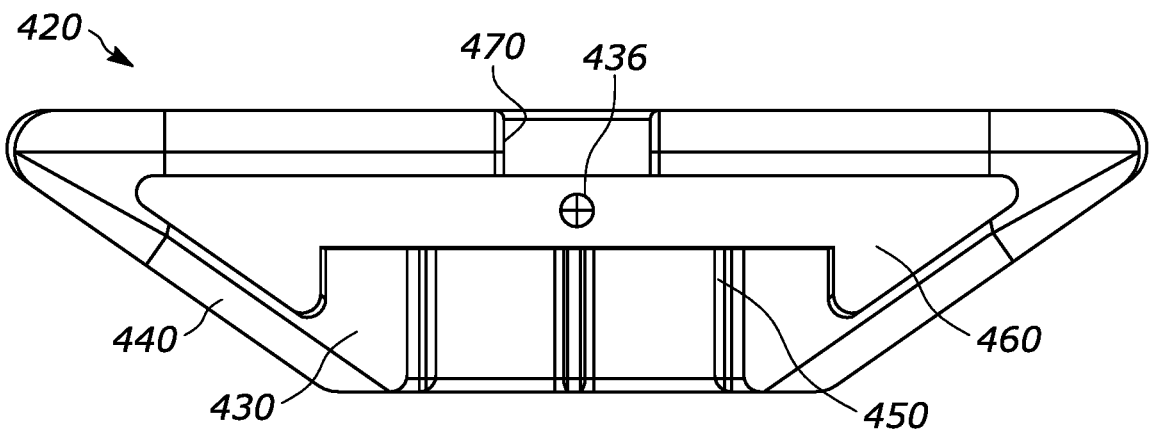
FIG. 5C is a front view of the backstop shown in FIG. 5A.
Figure 5D:
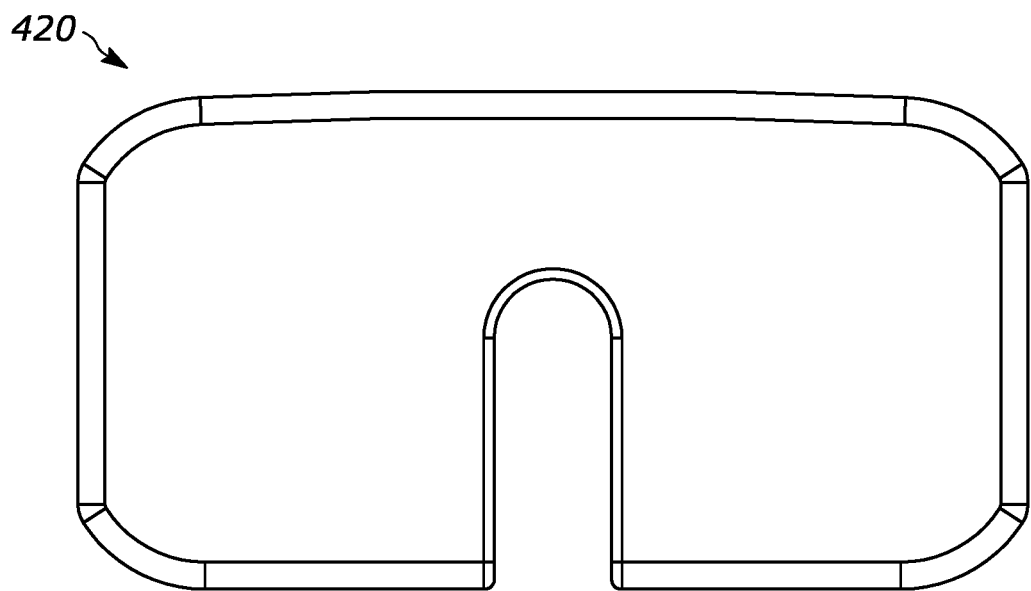
FIG. 5D is a top view of the backstop shown in FIG. 5A.
Figure 5E:
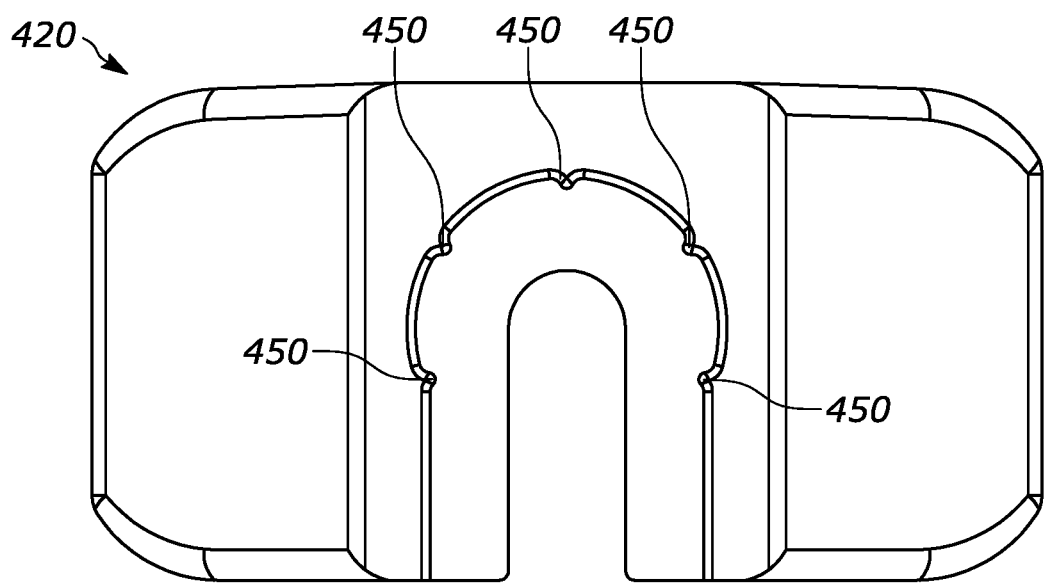
FIG. 5E is a bottom view of the backstop shown in FIG. 5A.

FIGS. 4A through 4B, show another exemplary backstop 320, which may be utilized with any suitable drug delivery device, for example a syringe such as syringe 10 shown in prior figures. The backstop 320 may generally include a collar portion 330 that extends around at least a portion of the syringe 10, an outer grip portion 340 for handling and/or gripping by the user, at least one protrusion such as a ridge 350 that helps permit or promote airflow through a space between the backstop and the syringe, a cavity 360 for receiving at least a portion of the syringe flange 12, and an opening 370 that permits the plunger rod 16 to extend through the backstop 320. The backstop 320 may include the features set forth in FIGS. 2A through 2H and the corresponding paragraphs describing the same, or other suitable features. Additionally, the backstop 320 further includes at least one protrusion 355 extending into the cavity 360. As a more specific example, the backstop 320 includes a plurality of nodules extending from opposing surfaces of the cavity. As an even more specific example, the backstop 320 shown in FIGS. 4A through 4B show eight total nodules, with four pairs designated by numerals 255a, 255b, 255c, and 255d. Each pair of nodules engages, abuts, and/or are positioned adjacent to various portions of the flange 12 to permit or promote airflow within the cavity 360. This configuration may avoid or minimize a space or a gap between upper and lower opposing surfaces defining the cavity 360, thereby potentially providing a more secure connection between the syringe 10 and the backstop 320, while also minimizing or reducing occluded air spaces.

FIGS. 5A through 5E, show another exemplary backstop 420, which may be utilized with any suitable drug delivery device, for example a syringe such as syringe 10 shown in prior figures. The backstop 420 may generally include a collar portion 430 that extends around at least a portion of the syringe 10, an outer grip portion 440 for handling and/or gripping by the user, at least one protrusion such as a ridge 450 that helps permit or promote airflow through a space between the backstop and the syringe, a cavity 460 for receiving at least a portion of the syringe flange 12, and an opening 470 that permits the plunger rod 16 to extend through the backstop 420. The backstop 420 may include the features set forth in FIGS. 2A through 2H and the corresponding paragraphs describing the same, or other suitable features. The collar 430 shown in FIG. 5A has a shorter height 438 (e.g. a length along axis 11d) than the collar height 138 shown in FIGS. 2A through 2H. As discussed above, a larger collar height may have some advantages and a shorter collar height may have other advantages, but both or either design may be suitable. The center of gravity of the backstop 420 is designated by numeral 436 in FIG. 5C. Also or alternatively, a shorter collar height 138 may be advantageous for users who prefer to hold the barrel with their fingers, rather than holding the backstop, because the shorter collar provides more access to the syringe barrel. As a more specific example, some users may prefer to grip the syringe by the barrel such that back of the user's finger(s) engage the the outer grip portion 440 rather than the front of the user's finger(s) engaging the outer grip portion 440.

Figure 6A:
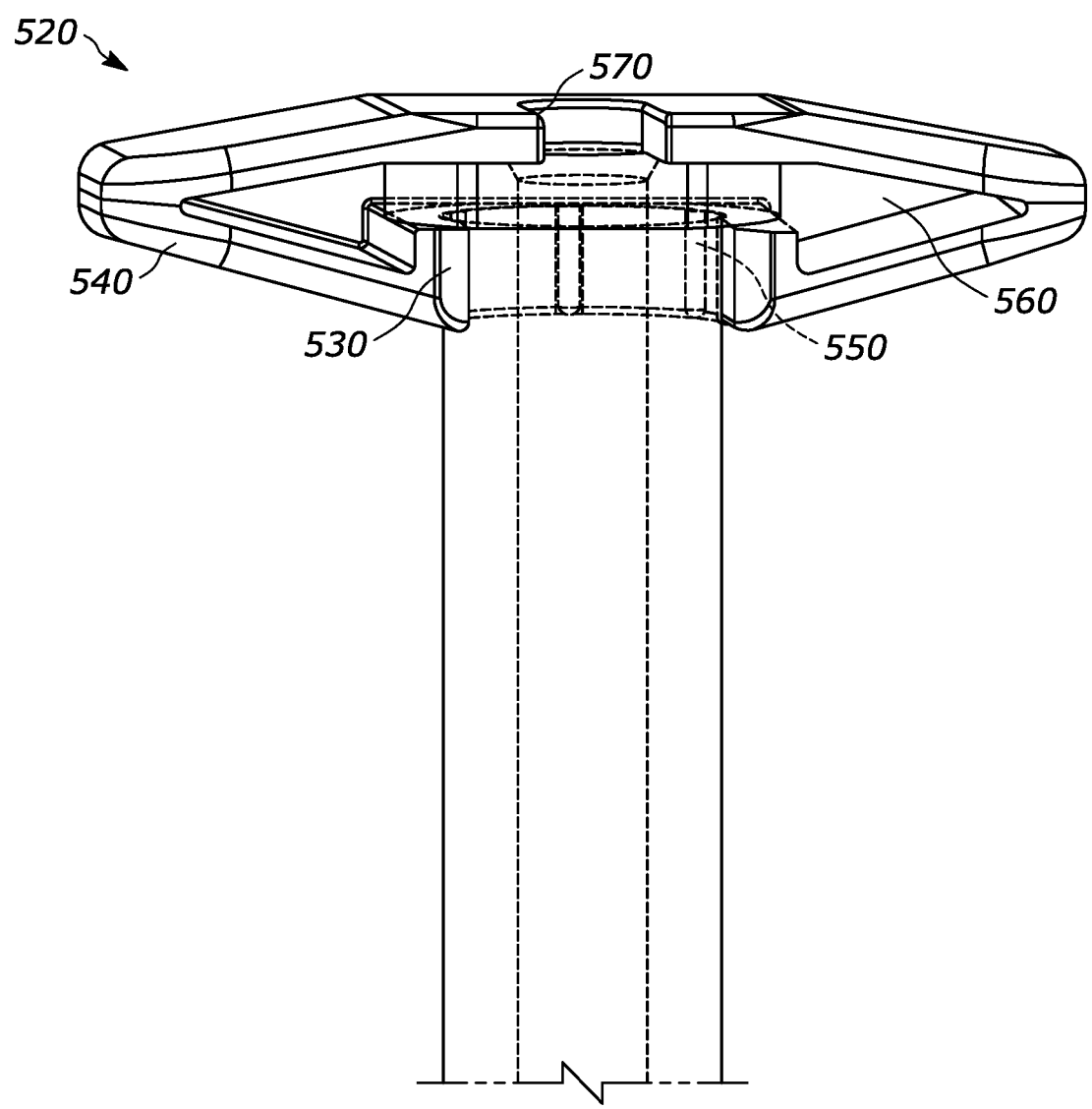
FIG. 6A is a perspective view of another exemplary injection device according to aspects of the present disclosure, and having a barrel (partially shown), a flange, and a backstop.
Figure 6B:
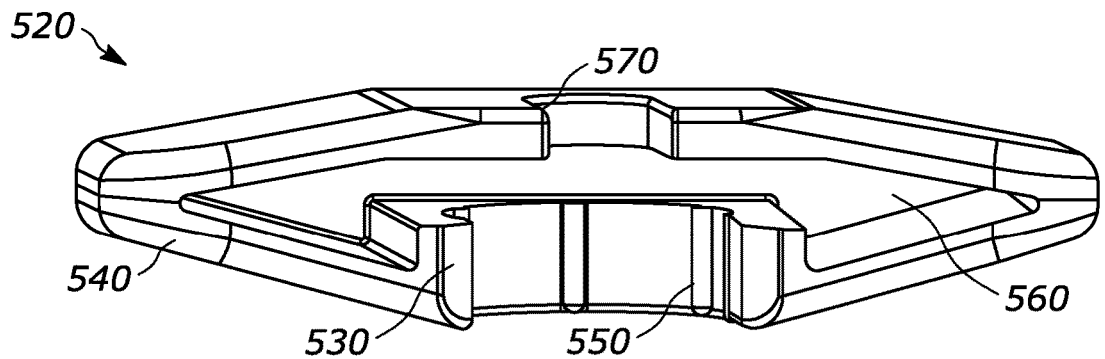
FIG. 6B is a perspective view of the backstop shown in FIG. 6A.
Figure 6C:
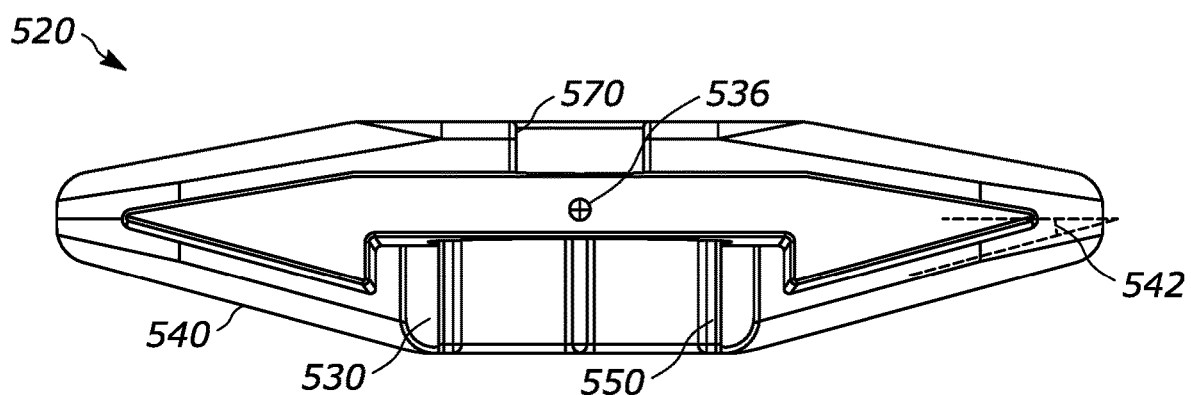
FIG. 6C is a front view of the backstop shown in FIG. 6A.
Figure 6D:
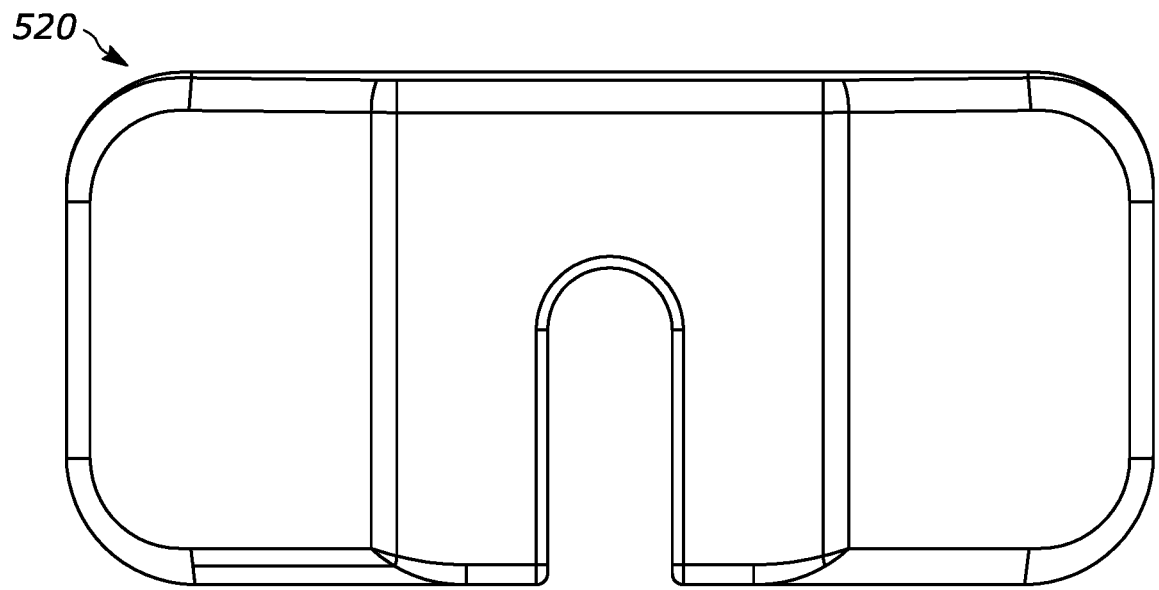
FIG. 6D is a top view of the backstop shown in FIG. 6A.
Figure 6E:
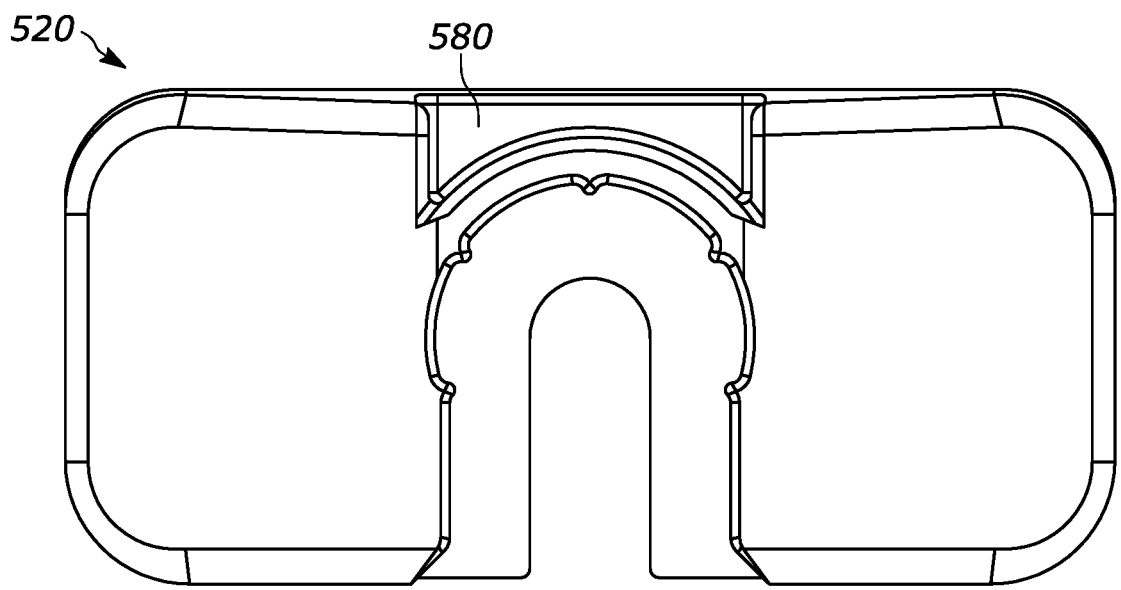
FIG. 6E is a bottom view of the backstop shown in FIG. 6A.

FIGS. 6A through 6E, show another exemplary backstop 520, which may be utilized with any suitable drug delivery device, for example a syringe such as syringe 10 shown in prior figures. The backstop 520 may generally include a collar portion 530 that extends around at least a portion of the syringe 10, an outer grip portion 540 for handling and/or gripping by the user, at least one protrusion such as a ridge 550 that helps permit or promote airflow through a space between the backstop and the syringe, a cavity 560 for receiving at least a portion of the syringe flange 12, and an opening 570 that permits the plunger rod 16 to extend through the backstop 520. The backstop 520 may include the features set forth in FIGS. 2A through 2H and the corresponding paragraphs describing the same, or other suitable features. The center of gravity of the backstop 520 is designated by numeral 536 in FIG. 6C. The outer grip portion 540 has an angle 542 of approximately negative 15 degrees with respect to a horizontal line (i.e. a line perpendicular to the axis). Therefore, the outer grip portion 540 has an angle of 105 degrees with respect to the syringe axis 11d. It may be desirable for the angle of the outer grip portion 540 with respect to the syringe axis 11d to be closer to 90 degrees than 180 degrees (i.e., 135 degrees or less) to allow the user to have a sufficient grip on the outer grip portion 540. It may be more desirable to have a smaller angle of the outer grip portion 540 with respect to the syringe axis 11d, such as 125 degrees or less, or 120 degrees or less, or 115 degrees, or 105 degrees, or less. The outer grip portion 540 may also include a non-slip or grip-enhancement feature such as ribs or a material with a relatively high coefficient of friction. As shown in FIG. 6E, the backstop 520 has a carveout portion 580 for reducing material costs and part weight.

Figure 7A:
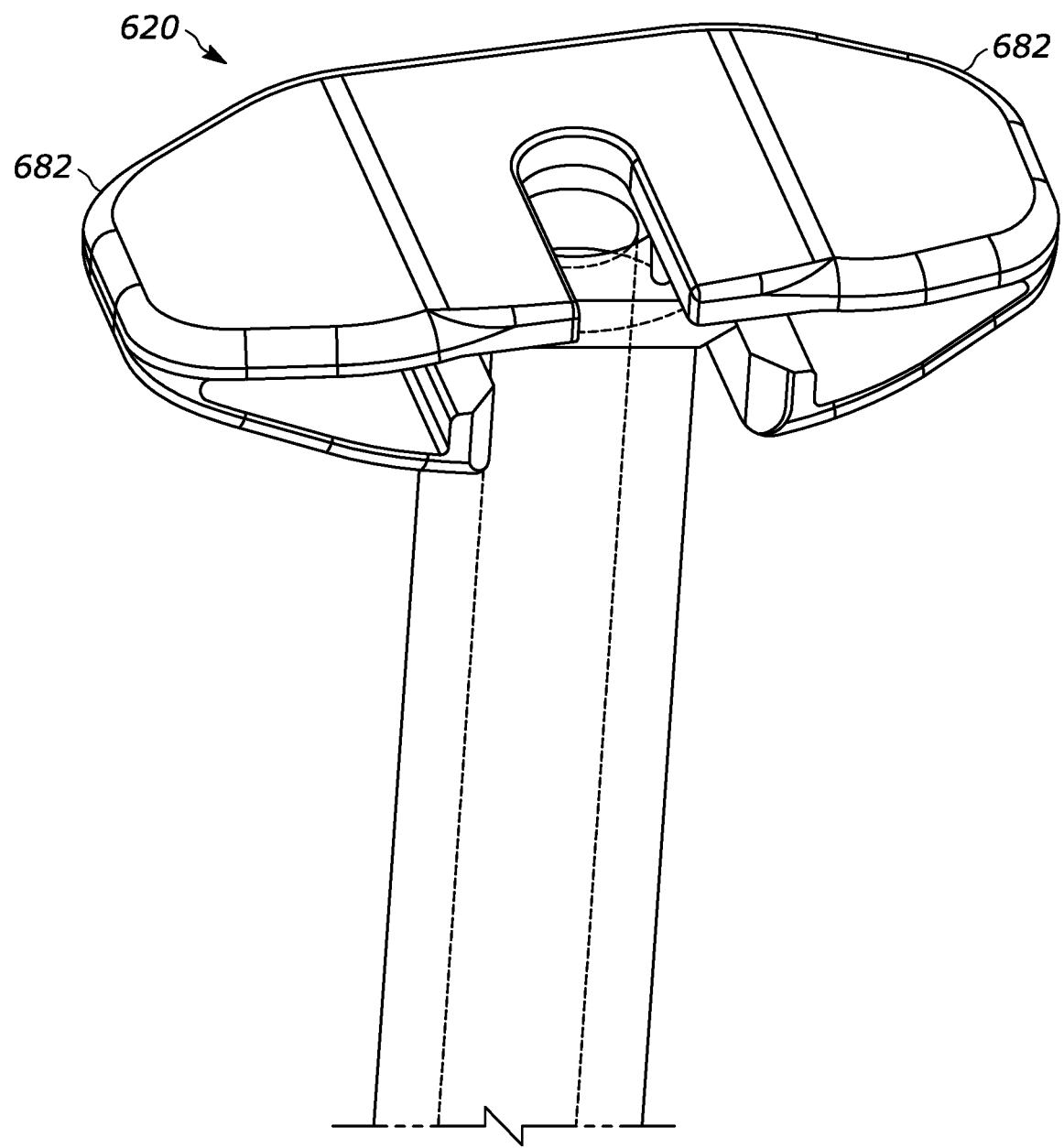
FIG. 7A is a perspective view of another exemplary injection device according to aspects of the present disclosure, and having a barrel (partially shown), a flange, and a backstop.
Figure 7B:
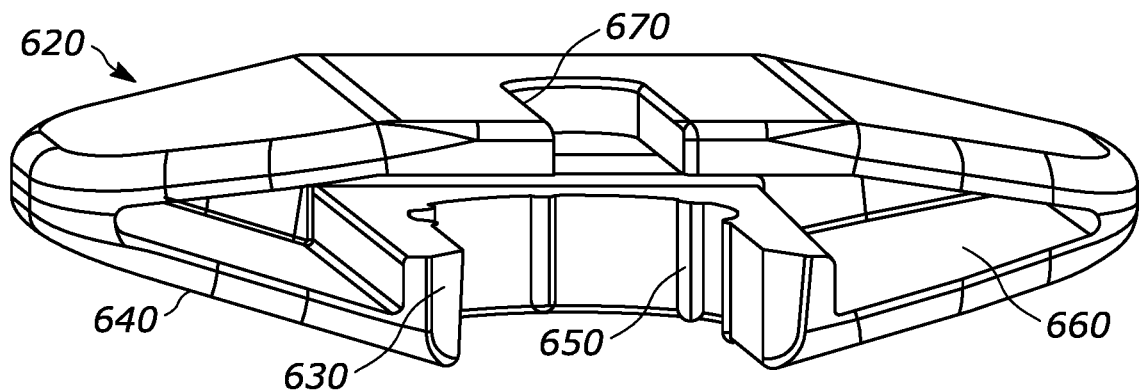
FIG. 7B is a perspective view of the backstop shown in FIG. 7A.
Figure 7C:
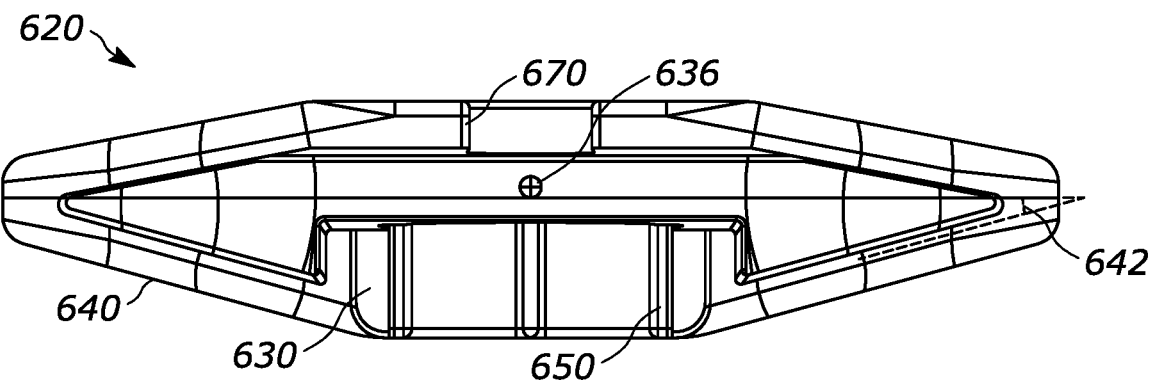
FIG. 7C is a front view of the backstop shown in FIG. 7A.
Figure 7D:
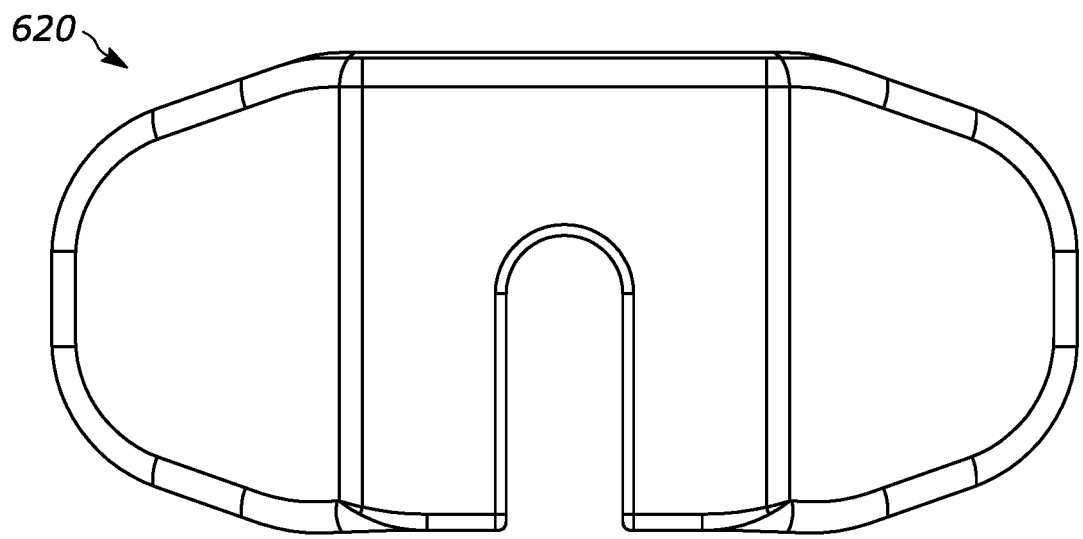
FIG. 7D is a top view of the backstop shown in FIG. 7A.
Figure 7E:
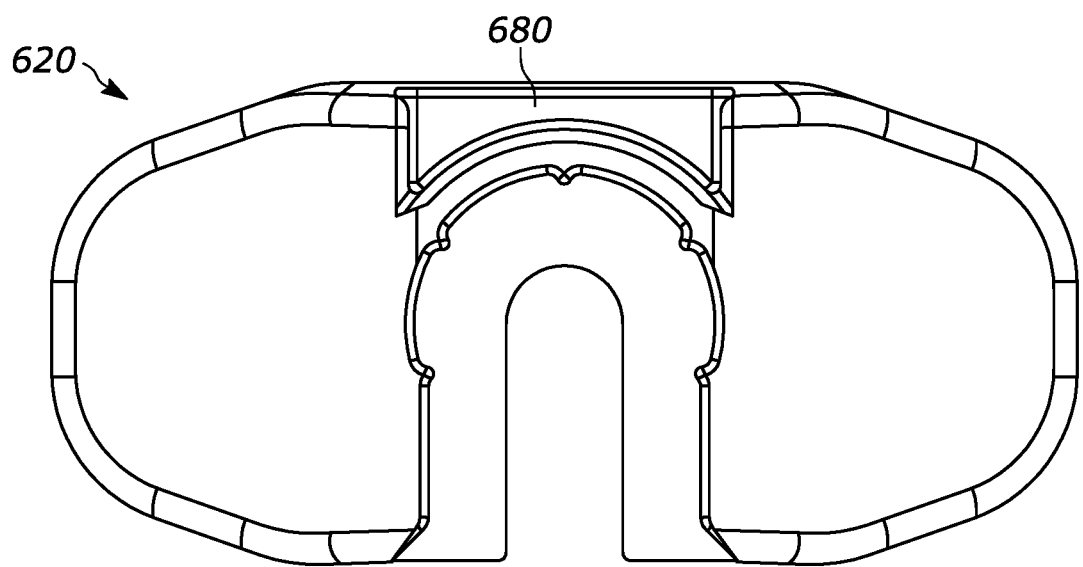
FIG. 7E is a bottom view of the backstop shown in FIG. 7A.

FIG. 7A show another exemplary backstop 620, which may be utilized with any suitable drug delivery device, for example a syringe such as syringe 10 shown in prior figures. The backstop 620 may generally include a collar portion 630 that extends around at least a portion of the syringe 10, an outer grip portion 640 for handling and/or gripping by the user, at least one protrusion such as a ridge 650 that helps permit or promote airflow through a space between the backstop and the syringe, a cavity 660 for receiving at least a portion of the syringe flange 12, and an opening 670 that permits the plunger rod 16 to extend through the backstop 620. The backstop 620 may include the features set forth in FIGS. 2A through 2H and the corresponding paragraphs describing the same, or other suitable features. The center of gravity of the backstop 620 is designated by numeral 636 in FIG. 7C. The outer grip portion 640 has an angle 642 of approximately negative 15 degrees with respect to a horizontal line (i.e. a line perpendicular to the axis). Therefore, the outer grip portion 640 has an angle of 105 degrees with respect to the syringe axis 11d. It may be desirable for the angle of the outer grip portion 640 with respect to the syringe axis 11d to be closer to 90 degrees than 180 degrees (i.e., 135 degrees or less) to allow the user to have a sufficient grip on the outer grip portion 640. It may be more desirable to have a smaller angle of the outer grip portion 640 with respect to the syringe axis 11d, such as 125 degrees or less, or 120 degrees or less, or 115 degrees, or 105 degrees, or less. The outer grip portion 640 may also include a non-slip or grip-enhancement feature such as ribs or a material with a relatively high coefficient of friction. As shown in FIG. 7E, the backstop 620 has a carveout portion 680 for reducing material costs and part weight. The backstop 620 may be similar to the backstop 520 shown in FIGS. 6A through 6E, except that the top surface has a more tapered profile, as shown in the corners and indicated by numeral 682. The more tapered profile may be advantageous from an ergonomic, aesthetic, material cost, and/or part weight standpoint. As a more specific example, the tapered profile of the backstop 620 may provide the user with a feeling of more precision.

Figure 8A:
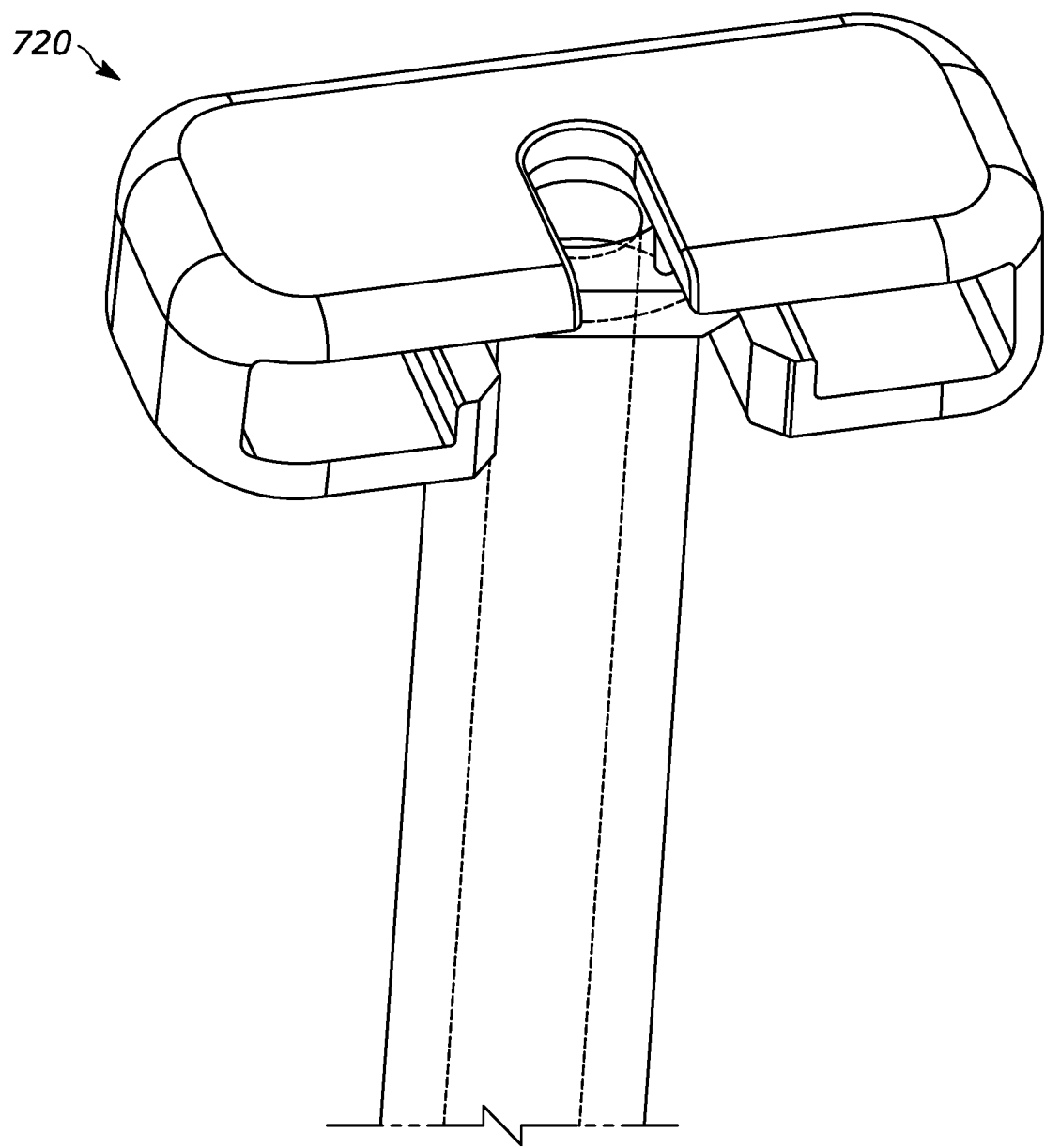
FIG. 8A is a perspective view of another exemplary injection device according to aspects of the present disclosure, and having a barrel (partially shown), a flange, and a backstop.
Figure 8B:
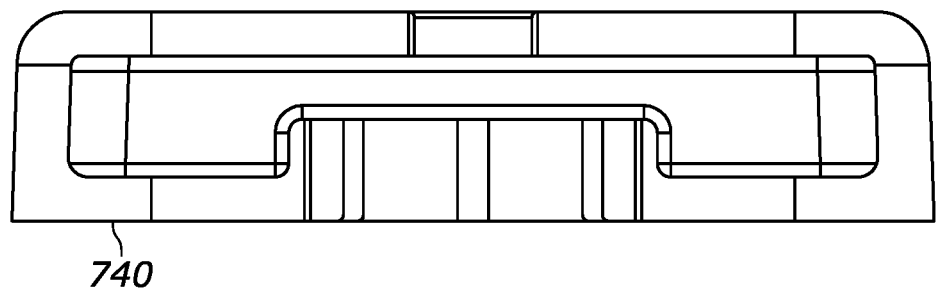
FIG. 8B is a front view of the backstop shown in FIG. 8A.
Figure 8C:
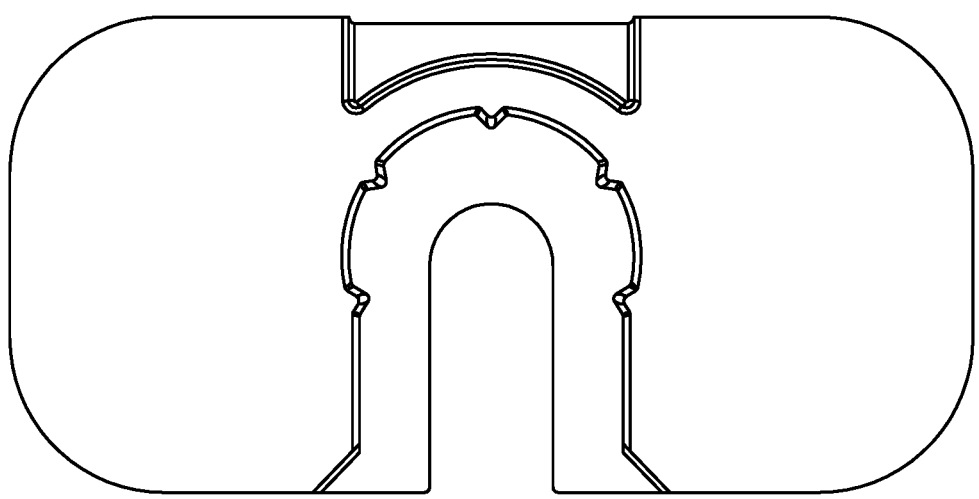
FIG. 8C is a top view of the backstop shown in FIG. 8A.
Figure 9A:
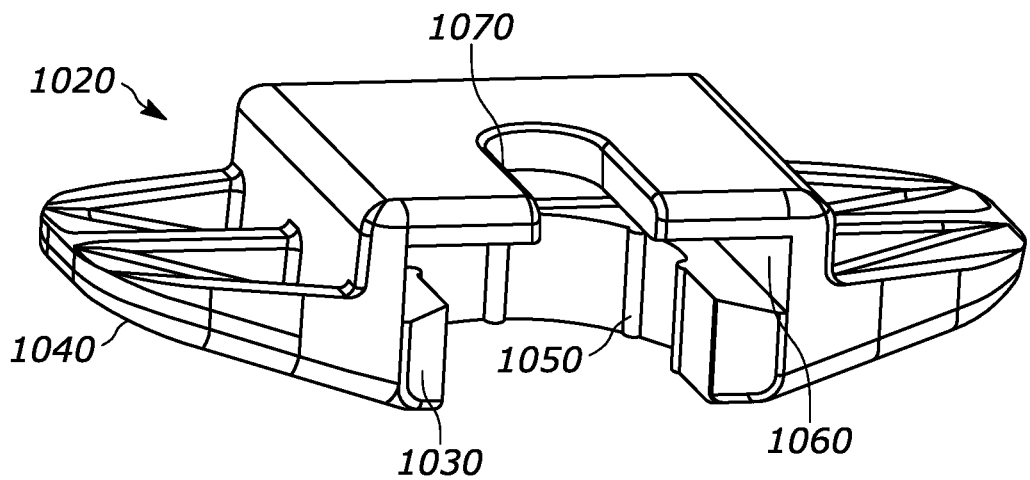
FIG. 9A is a perspective view of another exemplary injection device according to aspects of the present disclosure.
Figure 9B:
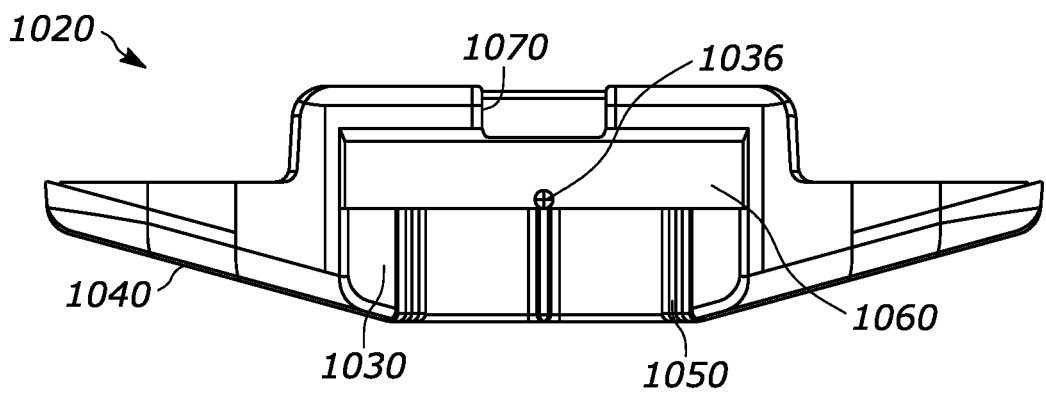
FIG. 9B is a front view of the backstop shown in FIG. 9A.
Figure 9C:
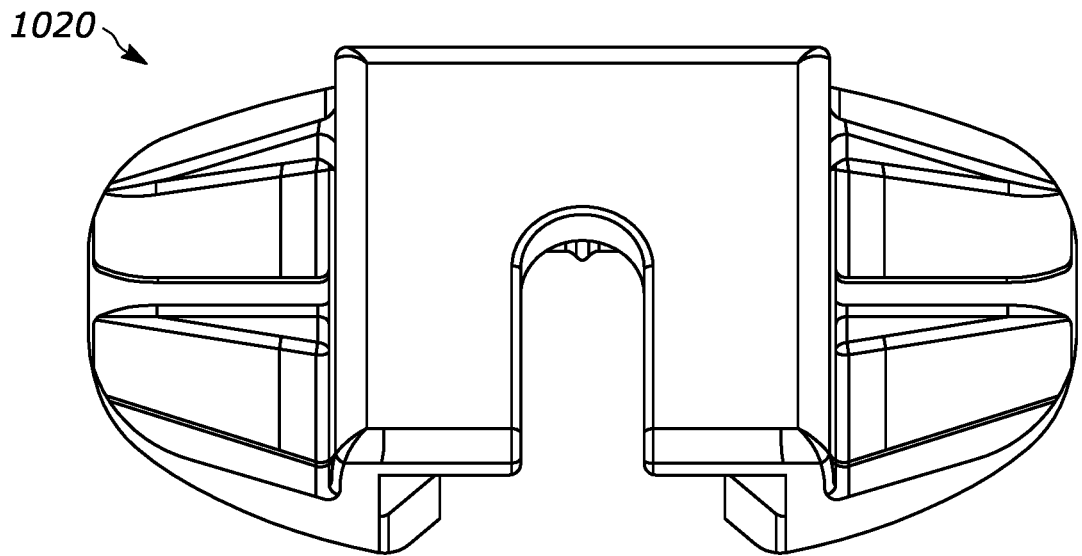
FIG. 9C is a top view of the backstop shown in FIG. 9A.
Figure 9D:
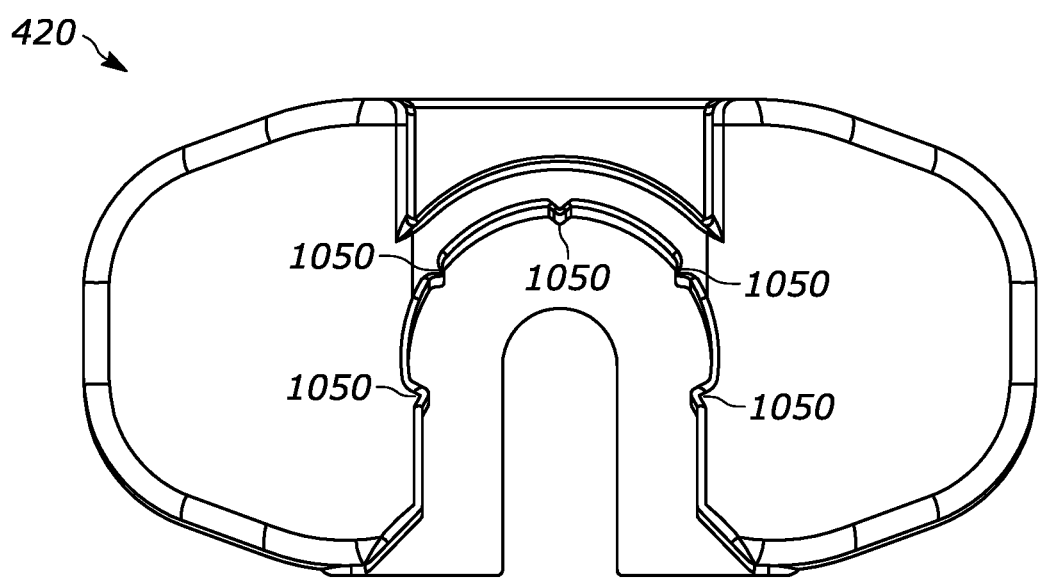
FIG. 9D is a bottom view of the backstop shown in FIG. 9A.

FIGS. 8A through 8C show another exemplary backstop 720, which may be utilized with any suitable drug delivery device, for example a syringe such as syringe 10 shown in prior figures. The backstop 720 may be similar to the backstop 120 shown in FIGS. 2A through 2H, except that the outer grip portion 740 has a more horizontal profile with respect to the syringe axis. The more horizontal profile may be advantageous from a grip standpoint.

FIGS. 9A through 9D, show another exemplary backstop 1020, which may be utilized with any suitable drug delivery device, for example a syringe such as syringe 10 shown in prior figures. The backstop 1020 may generally include a collar portion 1030 that extends around at least a portion of the syringe 10, an outer grip portion 1040 for handling and/or gripping by the user, at least one protrusion such as a ridge 450 that helps permit or promote airflow through a space between the backstop and the syringe, a cavity 1060 for receiving at least a portion of the syringe flange 12, and an opening 1070 that permits the plunger rod 16 to extend through the backstop 1020. The backstop 1020 may include the features set forth in FIGS. 2A through 2H and the corresponding paragraphs describing the same, or other suitable features. The center of gravity of the backstop 1020 is designated by numeral 1036 in FIG. 9B.

At least some of the backstops shown in the figures were tested in a lethality study. For example, pre-filled syringes were "spiked" with between $1 \times 10^{\wedge}6$ and $6 \times 10^{\wedge}6$ CFU (e.g., between 1,000,000 and 6,000,000 CFU) of *Geobacillus stearothermophilus* before sterilization cycles. As a more specific example, the backstop and barrel portions of the prefilled syringes were spiked with the $1$-$6 \times 10^{\wedge}6$ CFU of *Geobacillus stearothermophilus*. As used herein, the term "CFU" refers to "Colony-Forming Unit", which is a unit used to estimate the number of viable bacteria or fungal cells in a sample (where "viable" is the ability to multiply via binary fission under controlled conditions). *Geobacillus stearothermophilus* (previously *Bacillus stearothermophilus*) is a rod-shaped, gram-positive bacterium and a member of the division Firmicutes. The bacterium is a thermophile and is widely distributed in soil, hot springs, ocean sediment, and is a potential cause of spoilage in food products. The spiked pre-filled syringes were then sterilized using various sterilization parameters to measure the lethality of the sterilization process to evaluate the Sterility Assurance Level (SAL). The pre-filled syringes were spiked with biological indicators or direct inoculation, as is discussed in more detail below.

An exemplary method of assembling and externally sterilizing a drug delivery device according to an embodiment of the present disclosure is now described. During a first step, at least some individual components of a drug delivery device are sterilized, often prior to receipt by the manufacturing facility. For example, the syringe barrel and plunger stopper, and any other components that may have direct contact with the drug product, may be sterilized during this step. This step may utilize a variety of known techniques for sterilizing various unassembled components of the drug delivery device, including but not limited to components shown in the Figures. During a second step, the barrel is filled and the stopper (a.k.a. the "plunger stopper") is assembled with the barrel. The assembly step may also include adding at least some of the following: a plunger rod, a flange extender, a tip cap with Luer Lock, a needle, a rigid needle shield, and/or a backstop such as those shown in the Figures. At least some of these components may be pre-assembled with each other, but they may also be assembled at the filling line, such as if the filling process is performed aseptically. Also, the syringe typically will either have a tip cap Luer Lock tip or a mounted (e.g., staked) needle rather than having both components.

Next, the external sterilization steps proceed. First, the syringes are preconditioned. For a process utilizing Nitrogen Dioxide (NO2), preconditioning may include at least some or all of the following steps: removing the samples from storage, allowing the syringes to adjust to room condition equilibration for a desired amount of time (such as 30 minutes, 90 minutes, 2 hours, or any desirable amount of time), and placing the syringes into a sterilization chamber. Preconditioning may occur inside or outside of the chamber. When utilizing Ethylene Oxide (EtO), the precondition step may vary slightly than the step described for NO2. For example, the syringes may be preconditioned inside of the sterilization chamber (without gas injection) for 360 minutes (or another desirable length of time). However, as with the process utilizing NO2, the preconditioning step utilizing EtO may occur inside or outside of the chamber.

Next, the sterilization chamber is closed and all or substantially all of the air is evacuated from the chamber. Then the sterilization chamber is humidified to a desired setting, such as 75 or 80 (or any desired amount of percentage of relative humidity).

Next, the desired sterilization gas is injected and held in the chamber for a desired dwell time. For recipes utilizing NO2, the gas injection may include some or all of the following steps: delivering a dose of NO2 by pulling a vacuum in the chamber for a desired amount of time (i.e., dwell time) while injecting a desired amount of gas (dose concentration), purging the gas and release the vacuum, and then repeating these steps for a desired number of pulses. Once the number of desired pulses are complete, the gas is then finally purged so that the gas is removed from the sterilization chamber. Finally, the chamber is aerated for a desired number of cycles (a.k.a. "Aeration Exchanges") to ensure that all or substantially of the sterilization gas has been flushed from the syringe and packaging. The vacuum level may vary during these steps; for example the vacuum during dwell time may be minimal, such as approximately 590 Torr.

The method may include any suitable parameters for the above steps, such as:

The vacuum level may be between about 100 and 500 Torr, between about 150 and 400 Torr, between about 150 and 300 Torr, or another suitable vacuum level.

The concentration of the dose of the NO2 may be between about 2 and 20 milligrams per Liter, between about 2 and 10 milligrams per Liter, between about 2 and 7 milligrams per Liter, or another suitable concentration of the dose.

The chamber may have a relative humidity of between about 70 and 90 percent or another suitable humidity.

The dwell time may be between about 2 and 20 minutes, between about 2 and 12 minutes, between about 2 and 7 minutes, or another suitable dwell time.

The number of pulses may be between about 1 and 24, between about 1 and 12, between about 1 and 8, between about 1 and 4, between about 1 and 2, or another suitable number of pulses.

The step of aerating the sterilization chamber may include aerating the sterilization chamber a number of cycles between about 12 and 35 or another suitable number of cycles.

As a more specific example, Table 1 shows different variables for ten different exemplary recipes for sterilizing a drug delivery device utilizing Nitrogen Dioxide (NO2):

TABLE 1

| Vacuum (Torr) | NO2 Dose (mg/L) | Relative Humidity (%) | Dwell Time (mins.) | Number of Pulses | Number of Aerations |
|---|---|---|---|---|---|
| 20 | 10 | 75 | 10 | 8 | 28 |
| 20 | 20 | 80 | 20 | 4 | 24 |
| 20 | 10 | 80 | 20 | 4 | 24 |
| 20 | 10 | 80 | 10 | 4 | 24 |
| 20 | 10 | 80 | 10 | 2 | 24 |
| 20 | 10 | 80 | 10 | 1 | 24 |
| 20 | 5 | 80 | 10 | 1 | 24 |
| 20 | 5 | 80 | 10 | 2 | 24 |
| 20 | 5 | 80 | 5 | 2 | 24 |
| 500 | 5 | 80 | 5 | 2 | 70 |

As another example, Table 2 shows different variables for six different exemplary recipes for sterilizing a drug delivery device utilizing NO2:

TABLE 2

| Vacuum (Torr) | NO2 Dose (mg/L) | Relative Humidity (%) | Dwell Time (mins.) | Number of Pulses | Number of Aerations |
|---|---|---|---|---|---|
| 20 | 10 | 75 | 10 | 8 | 12 |
| 20 | 10 | 75 | 10 | 12 | 12 |
| 20 | 10 | 75 | 10 | 24 | 12 |
| 100 | 10 | 75 | 10 | 8 | 12 |
| 100 | 10 | 75 | 10 | 12 | 12 |
| 100 | 10 | 75 | 10 | 24 | 12 |

In Tables 1 and 2, the "Vacuum Level (Torr)" column label refers to the vacuum force applied on the external sterilization chamber during step 4 in FIG. 1. As shown, the vacuum force varies from 20 Torr to 500 Torr, although different vacuum forces may be appropriate. The vacuum force numbers listed are inverse to their strength, such that a 20 Torr force is stronger than a 100 Torr force, which is stronger than a 500 Torr force (ambient pressure is typically about 760 Torr). The stronger the vacuum force, the greater the chance of demonstrating kill of the target bioburden. However, if the vacuum force becomes too high, then the process may result in undesirable effects on the medicament, such as causing the plunger to move undesirably (i.e. to move past the sterility barrier and cause a sterility breach). The "NO2 Dose (mg/L)" column refers to the concentration (in mg) of NO2 per liter of air introduced to the external sterilization chamber. As shown, the dose in Tables 1 and 2 varies between 5 and 20 mg/L, although different doses may be appropriate. The higher the dose of NO2 during this step, the faster and more completely the drug delivery device will be sterilized. However, if the dose of sterilization gas becomes too high, then the process may result in undesirable effects on the medicament, such as contaminating the inside of the drug barrel with sterilization gas (i.e., ingress of sterilization gas and/or discoloration of the syringe components). The "Relative Humidity (% RH)" column refers to the relative humidity in the external sterilization chamber. As shown, the relative humidity for each row in Tables 1 and 2 varies between 75% and 80%, although different relative humidity values may be appropriate. Increasing the relative humidity also increases the likelihood of demonstrating kill of the target bioburden. The "Dwell Time (mm:ss)" column refers to the amount of time that the drug delivery device sits in the sterilization chamber while sterilization gas is present. For Tables 1 and 2, the "Total Dwell Time" is equal to the "Dwell Time" column times the "Number of Pulses" column. For example, for the first row of Table 1, the samples would experience a Total Dwell Time of 80 minutes. As shown, the dwell times listed in Tables 1 and 2 vary between 5 and 20 minutes, although different dwell times may be appropriate. The dwell time also increases the likelihood of demonstrating kill of the target bioburden. However, if the dwell time becomes too high, then the process may result in undesirable effects on the medicament, such as contaminating the inside of the drug barrel with sterilization gas. The "Number of Pulses" column refers to the number of times during the NO2 process that the gas is injected by pulling a vacuum. As shown, the pulses for each row in Tables 1 and 2 varies from 1 to 24, although different values may be appropriate. The higher the number of pulses, the greater the chance of demonstrating kill of the target bioburden. However, if the number of pulses becomes too high, then the process may result in undesirable effects on the medicament, such as contaminating the inside of the drug barrel with sterilization gas. The column referring to "Number of Aerations" refers to the number of times that the chamber is aerated after the gas is purged from the chamber. The exemplary process may utilize aeration exchanges of 12, 24, 28, 70, or any desirable number. Up to a certain point, by increasing the number of aerations, the manufacturer may increase the likelihood that all or substantially all of the sterilization gas is removed from the syringe and packaging (post-purge).

For each of the recipes in Tables 1 and 2 (NO2), each of the steps contained within box 1 in FIG. 1 may be performed at room temperature (25 degrees Celsius), but other appropriate temperatures may be used. However, other temperatures may be used, such as between about 2 degrees Celsius to about 8 degrees Celsius, or any other desirable temperature that does not undesirably affect the medicament.

Table 3 shows different variables for 10 different exemplary recipes for sterilizing a drug delivery device utilizing NO2:

TABLE 3

| Vacuum (Torr) | NO2 Dose (mg/L) | Relative Humidity (%) | Dwell Time (mins.) | Number of Pulses | Number of Aerations |
|---|---|---|---|---|---|
| 100 | 10 | 75 | 10 | 2 | 24 |
| 300 | 10 | 75 | 10 | 2 | 35 |
| 100 | 20 | 80 | 20 | 4 | 24 |
| 20 | 10 | 80 | 10 | 4 | 24 |
| 100 | 10 | 75 | 10 | 2 | 24 |
| 100 | 20 | 80 | 20 | 4 | 24 |
| 20 | 10 | 80 | 10 | 4 | 24 |
| 300 | 10 | 75 | 10 | 2 | 35 |
| 20 | 10 | 80 | 10 | 4 | 24 |
| 20 | 20 | 80 | 20 | 4 | 24 |

When utilizing Ethylene Oxide (EtO), the gas injection step varies slightly. For example, the gas injection step may include some or all of the following steps: delivering a dose of EtO by pulling a vacuum in the chamber for a desired amount of time (i.e., dwell time) while injecting a desired amount of gas (dose concentration), and then purging the gas. In other words, when utilizing EtO, it may be desirable to run only one pulse rather than the preferred multiple pulses discussed above for NO2. For the steps of gas purge aeration, the exemplary process utilizing EtO proceeds as described above with respect to NO2.

Notably, different backstops such as the backstops disclosed herein were tested in the lethality study. Table 4 shows results of the lethality study evaluating the effects of NO2 based sterilization on various pre-filled syringes with backstops without protrusions and with protrusions:

TABLE 4

| Recipe Number | Vacuum (Torr) | NO2 Dose (mg/L) | Relative Humidity (%) | Dwell Time (mins.) | Number of Pulses | Number of Aerations | Spiked Backstop | Spiked Barrel |
|---|---|---|---|---|---|---|---|---|
| PFS Samples Utilizing Backstops Without Protrusions ||||||||| 
| 1 | 100 | 10 | 75 | 10 | 2 | 24 | 1/5 | 5/5 |
| 2 | 300 | 10 | 75 | 10 | 2 | 35 | 0/5 | 5/5 |
| 3 | 100 | 20 | 80 | 20 | 4 | 24 | 0/5 | 5/5 |
| 4 | 20 | 10 | 80 | 10 | 4 | 35 | 2/5 | 5/5 |
| PFS Samples Utilizing Backstops With Protrusions |||||||||
| 5 | 20 | 10 | 75 | 10 | 8 | 28 | 5/5 | 5/5 |
| 6 | 20 | 20 | 80 | 20 | 4 | 24 | 5/5 | — |
| 7 | 20 | 10 | 80 | 20 | 4 | 24 | 5/5 | — |
| 8 | 20 | 10 | 80 | 10 | 4 | 24 | 5/5 | — |
| 9 | 20 | 10 | 80 | 10 | 2 | 24 | 5/5 | — |
| 10 | 20 | 10 | 80 | 10 | 1 | 24 | 5/5 | 5/5 |
| 11 | 20 | 5 | 80 | 10 | 1 | 24 | 5/5 | 4/5 |
| 12 | 20 | 5 | 80 | 10 | 2 | 24 | 5/5 | 5/5 |
| 13 | 20 | 5 | 80 | 5 | 2 | 24 | 5/5 | 5/5 |
| 15 | 500 | 5 | 80 | 5 | 2 | 70 | 5/5 | 5/5 |

For each recipe number, five samples (or at least 5 test locations on one or more samples) were tested. Table 4 shows, in the "Spiked Backstop" and "Spiked" Barrel" columns, how many out of the 5 samples reached the target lethality for each recipe. For example, the target lethality for this test was a Sterility Assurance Level (SAL) of 10^6. In other words, the target lethality for this test was 6 logs reduction in the number of bacteria present (before sterilization vs. after sterilization). As a more specific example, for Recipe Number 1, one of the five samples tested reached this target lethality for the backstop area (Col. "Spiked Backstop", row corresponding with Recipe Number 1), but all five of the samples tested reached this target lethality for the barrel area (Col. "Spiked Barrel", row corresponding with Recipe Number 1). It should be noted that the spiked backstop test results for Recipe Nos. 1-4 (utilizing a backstop without protrusions) were tested via direct inoculation whereas the spiked backstop test results for Recipe Nos. 5-14 (utilizing the backstop 120 or 220, shown in FIGS. 3-4) were tested via biological indicators. It also should be noted that "-" symbols indicate that no data is reported for those parameters/samples. The testing method variance aside, the samples tested utilizing backstops with protrusions achieved target lethality at a much higher rate than the samples utilizing the backstop without protrusions. As discussed above, the ridges minimize and/or prevent occluded spaces and instead permit the sterilization agent to completely or substantially reach various components of the pre-filled syringe, particularly the backstop and flange areas.

Different sterilization parameters were also tested with respect to an ingress study. As discussed above, although it is desirable to achieve a target lethality during external sterilization, it is also desirable to reduce, minimize, and/or substantially prevent ingress of the sterilization gas into the drug product chamber. However, the two goals (achieving lethality and minimizing ingress) may serve as competing or counteracting interests. For example, some sterilization parameters that may improve the likelihood of achieving a higher lethality rate may increase the likelihood of having a higher ingress of sterilization gas. Table 5 below show results of an ingress study evaluating the effects of different recipes for NO2 based sterilization on the drug product chamber.

TABLE 5

| | Process Parameters ||||||  NO2 Content in Product (PPM) ||||
|---|---|---|---|---|---|---|---|---|---|---|
| Test No. | Vac. (Torr) | NO2 Dose (mg/L) | Rel. Hum. (%) | Dwell Time (mins.) | No. of Pulses | No. of Aerat. | Day 1 | Day 14 | Day 30 | Control |
| 1 | 300 | 10 | 75 | 10 | 4 | 35 | 0.157 | — | 0.182 | — |
| 2 | 300 | 10 | 75 | 10 | 8 | 35 | 0.167 | — | 0.404 | — |
| 3 | 20 | 10 | 75 | 10 | 8 | 24 | 0.343 | 0.350 | 0.417 | 0.350 |
| 4 | 20 | 10 | 75 | 10 | 16 | 24 | 0.387 | 0.358 | 0.450 | 0.384 |
| 5 | 20 | 10 | 75 | 10 | 24 | 24 | 0.342 | 0.431 | 0.403 | 0.336 |
| 6 | 100 | 10 | 75 | 10 | 8 | 24 | 0.346 | 0.345 | 0.360 | 0.344 |
| 7 | 100 | 10 | 75 | 10 | 16 | 24 | 0.351 | 0.404 | 0.391 | 0.348 |
| 8 | 100 | 10 | 75 | 10 | 24 | 24 | 0.375 | 0.370 | 0.394 | 0.355 |
| 9 | 300 | 10 | 75 | 10 | 8 | 35 | 0.369 | 0.398 | 0.344 | 0.362 |
| 10 | 300 | 10 | 75 | 10 | 16 | 35 | 0.366 | 0.430 | 0.408 | 0.362 |
| 11 | 300 | 10 | 75 | 10 | 24 | 35 | 0.378 | 0.804 | 1.132 | 0.368 |

The last four columns to the right (collectively labeled "NO2 Content in Product (PPM)") refers to the content of NO2 that ingress into the drug product container, more specifically the content of NO2 that ingress into the drug container, more specifically the NO2 level measured as part per million nitrate in the liquid. The first three columns in this group, labeled, "Day 1", "Day 14", and "Day 30" refer to the ingress as measured at different times after the sterilization process. The last column in this group, labeled "Control", refers to the base level of nitrates (NO3), which is a product of the NO2 and the samples (water for injection). When compared against the Day 1, etc. "exposed" samples, the control "non-exposed" samples provides a baseline differentiation between the exposed sample and the control. For example, for test no. 5, the ingress for day 1 is 0.342 and the control is 0.336, so the difference between an exposed and non-exposed sample may be 0.006 PPM. As another, potentially related parameter, the test method may have an error rate of +/−0.1 PPM.

Although it may be generally desirable to minimize or to substantially or completely prevent ingress, it may be desirable to avoid exceeding an ingress content of 3 PPM, 1 PPM, or another suitable limit. It may be desirable to utilize the "raw" Day 30 values, such as those listed in the column in Table 5 above, or it may be desirable to utilize the "corrected" Day 30 values that have been adjusted based on the Control values. As shown above in Table 5, almost all of the ingress values are below the threshold of 1 PPM (the only exception is the day 30 measurement for Sample 11). As is also shown in the above Table 5, varying the different vacuum forces, number of pulses, and number of aerations has varying effects on the ingress measurements. Utilizing these parameters and trends, one may be able to determine sterilization parameters that accomplish a target lethality while staying below a desired ingress level.

Figure 10A:
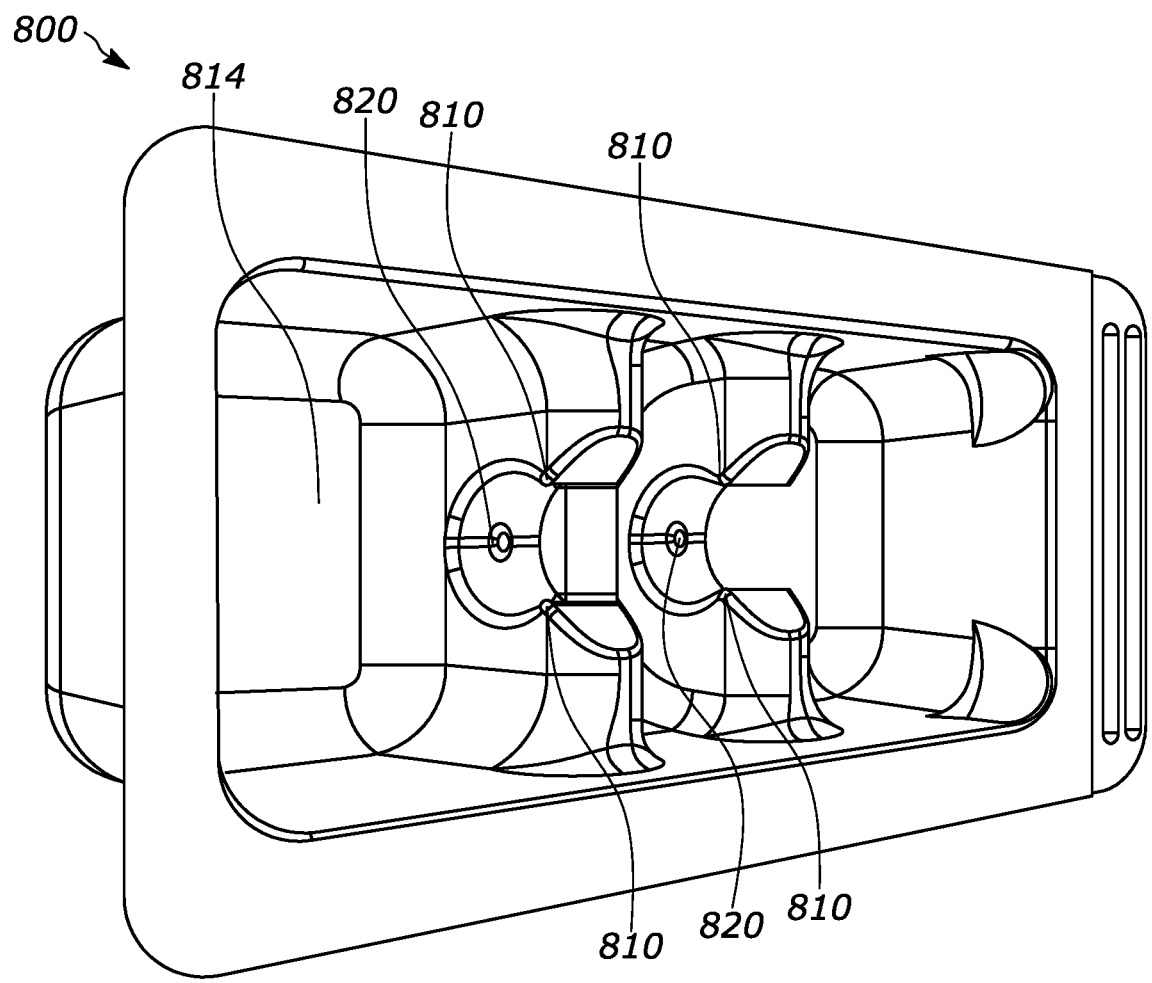
FIG. 10A is a perspective top view of an exemplary packaging according to aspects of the present disclosure, and that may be used for securing and/or holding an injection device, such as during external sterilization of the injection device.
Figure 10B:
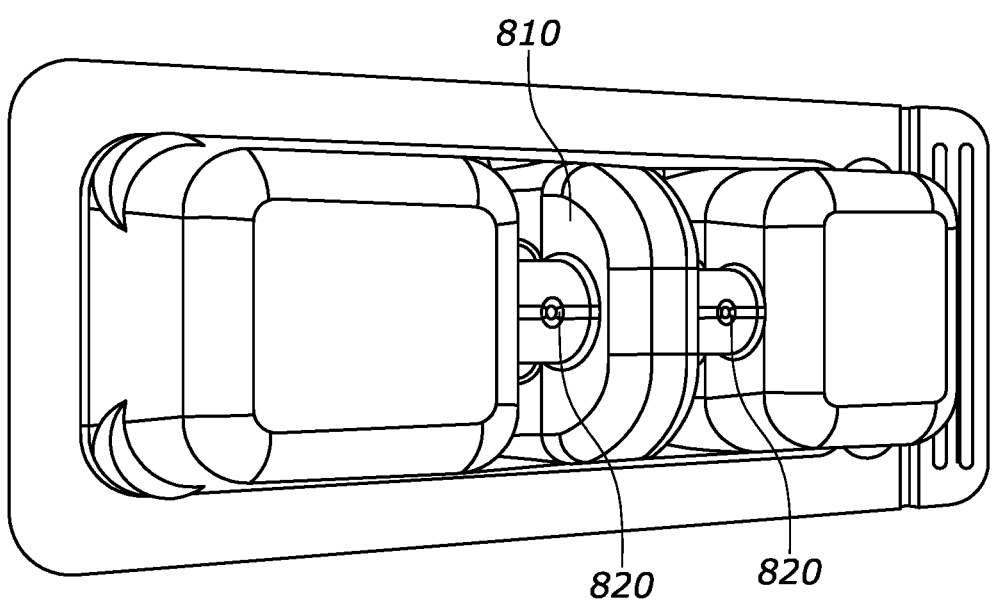
FIG. 10B is a perspective bottom view of the packaging shown in FIG. 10A.
Figure 10C:
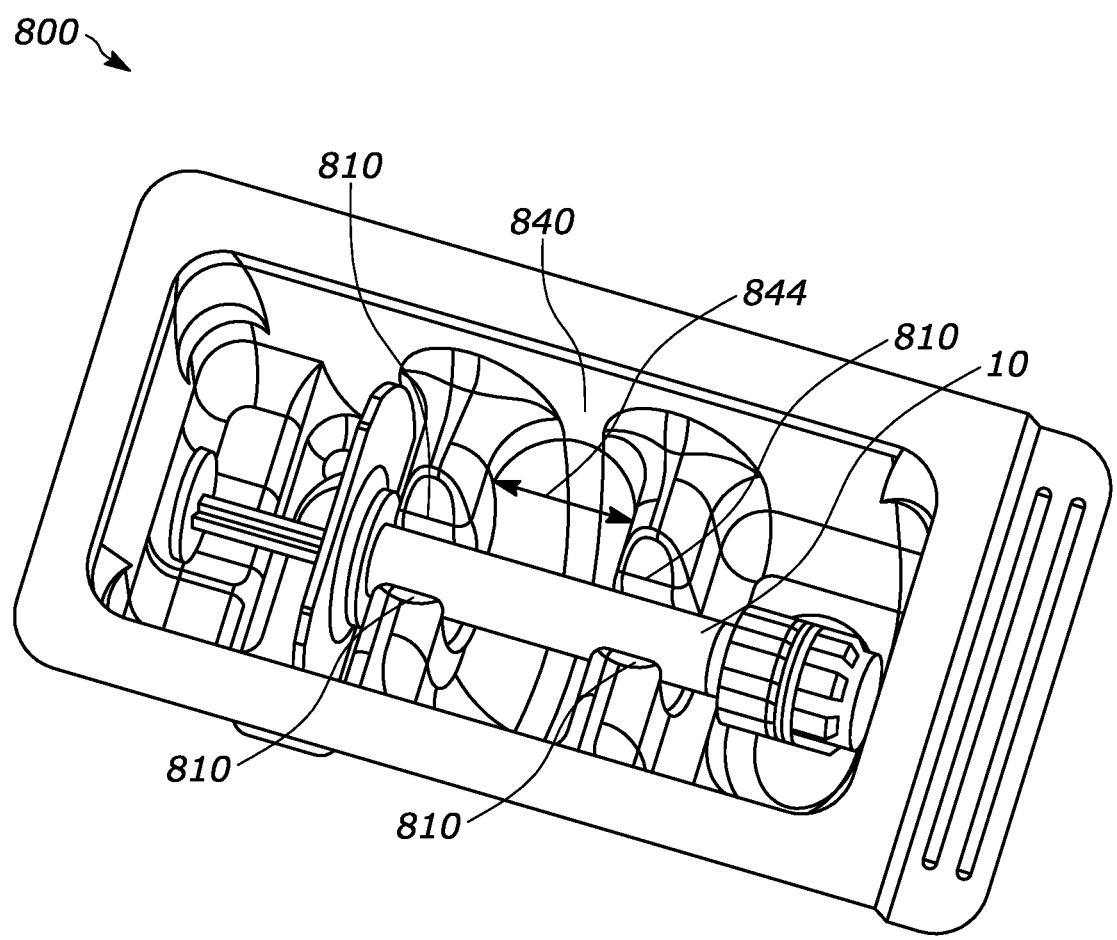
FIG. 10C is a perspective top view of the packaging shown in FIG. 10 with an exemplary injection device.

FIGS. 10A through 10C show packaging 800 for an injection device according to another embodiment of the present disclosure. The packaging 800 includes support walls 810 for receiving and supporting an injection device, such as a syringe 10 shown in other figures. The packaging 800 may be utilized during various steps in the life cycle of the injection device, including during at least one or more of the following steps: external sterilization, transport to the user, pre-use storage by the user, preparation of the injection device and the injection site for use, and post-injection storage. For example, at a manufacturing site a manufacturer may place an assembled pre-filled syringe (for example, a syringe barrel, a backstop, stopper, plunger rod, drug, and protective cap) into the packaging such that the assembled pre-filled syringe is supported by the packaging 800 in a snap-fit connection between the support walls 810 and the syringe barrel. The manufacturer may perform external sterilization steps on the assembled pre-filled syringe while the assembled pre-filled syringe is supported by the packaging 800. The manufacturer may also then add a protective coating (not shown) over the top wall 812 of the packaging to form an air-tight seal and to define a chamber 814 within the packaging 800 that protects the assembled pre-filled syringe from outside air and/or contaminants. The protective coating may be a transparent plastic layer coupled to the packaging 800 through any suitable means such as an adhesive and/or a heat-sealing step. During another step in the life cycle of the injection device, a user may peel away the protective coating to gain access to the pre-filled syringe.

The packaging 800 may include protrusions or spacers to limit surface area contact between the tray and the injection device, thereby reducing or preventing occluded spaces therebetween. For example, the packaging 800 may include protrusions 820 extending outward from the support walls 810 of the packaging 800 to create a gap between the injection device and the packaging 800, thereby minimizing or preventing occluded spaces between the same. Thereby, the protrusions or spacers permit an effective connection between the packaging and the injection device while allowing sterilization gas to flow in between the respective components during external sterilization steps. The protrusions or spacers may also improve aeration (reduced time and/or improved effectiveness) of the sterilization gas after the external sterilization step. The packaging 800 shown in FIGS. 10A through 10C includes two protrusions 820, but any suitable number may be utilized. Also, the protrusions 820 shown in FIGS. 10A through 10C have a generally pyramid shape but may have any suitable shape. As another example, the packaging 800 may not include a snap-fit arrangement with the syringe and may instead allow the syringe to rest therewithin to allow sterilization gas to flow in between the respective components during external sterilization steps. In such a design, the gaps between the support walls 810 would be larger than the diameter of the syringe to allow space between the support walls 810 and the syringe. Also, in such a design, the Tyvek cover would preferably prevent the syringe from moving out of the packaging.

The packaging 800 includes a center section 840 of the cavity (between two snap fit areas 810) that is wider than other known center sections. For example, the distance 844 shown in FIG. 10C is preferably at least 1.5 centimeters to allow space for the user to grip the syringe 10 when removing the same from the packaging 800. Even more preferably, the distance 844 shown in FIG. 10C is preferably at least 2.0 centimeters. Even more preferably, the distance 844 shown in FIG. 10C is preferably at least 2.5 centimeters. Even more preferably, the distance 844 shown in FIG. 10C is preferably at least 3.0 centimeters. Even more preferably, the distance 844 shown in FIG. 10C is preferably at least 4.0 centimeters. Even more preferably, the distance 844 shown in FIG. 10C is preferably at least 5.0 centimeters. Even more preferably, the distance 844 shown in FIG. 10C is preferably at least 6.0 centimeters.

Figure 11:
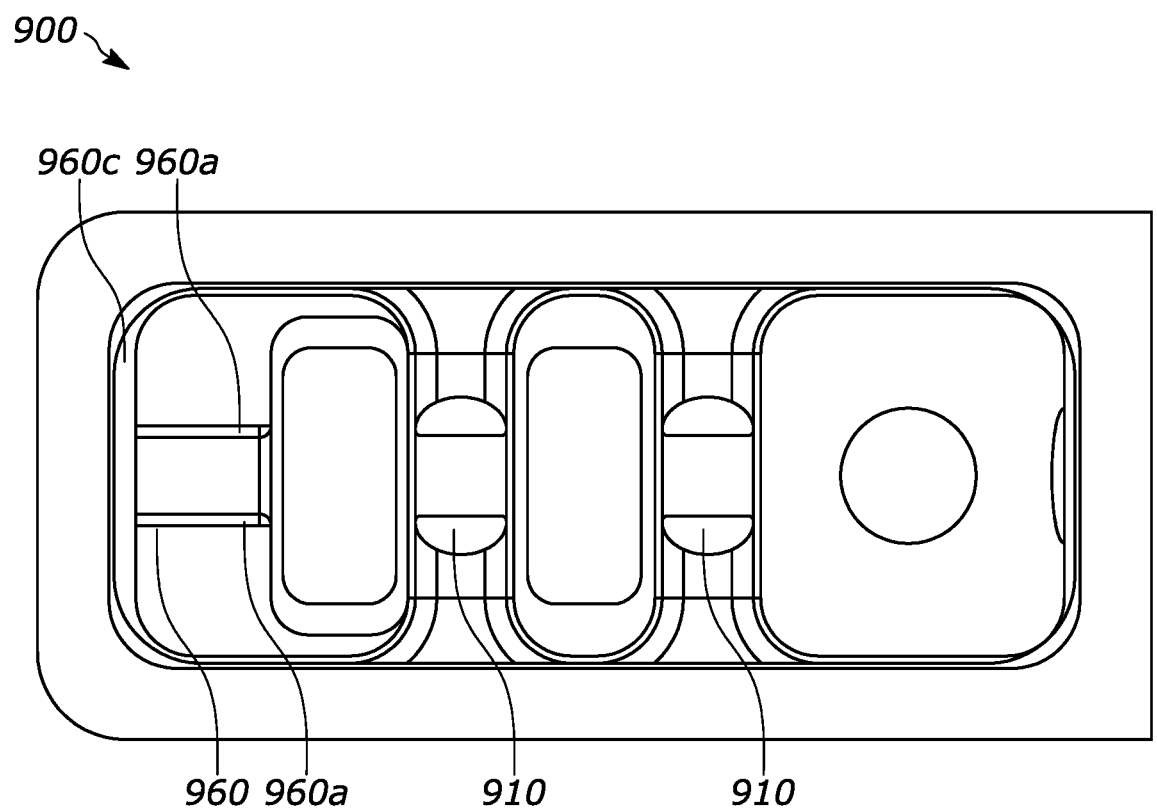
FIG. 11 is a perspective top view of another exemplary packaging according to aspects of the present disclosure, that may be used for securing and/or holding an injection device, such as during external sterilization of the injection device.

FIG. 11 shows packaging 900 for an injection device according to another embodiment of the present disclosure. For example, the packaging 900 includes a raised wall section 960 positioned near the portion of the packaging 900 that receives the plunger rod that secures the injection device plunger rod and/or prevents unintended movement of the injection device plunger. For example, the packaging 900 shown in FIG. 11 includes support walls 910 similar to those shown in FIGS. 10A-10C for receiving and supporting the barrel of the syringe 10. However, the packaging 900 shown in FIG. 11 also includes a raised wall section 960 that has side walls 960a for receiving and supporting the plunger rod 16 and another wall 960c that extends generally perpendicular to the support walls 910 and the side walls 960a such as to receive the plunger rod end 14 and to prevent and/or restrict distal movement of the plunger rod end 14 (and the entire plunger rod 16) until the syringe 10 has been removed from the packaging 900.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

Preferably, the pre-filled syringe does not include an internal coating. The syringe may also comprise a coating on the outer surface of the syringe which is in contact with the environment such as an oxygen barrier coating.

The syringe barrel may have a length of 45 to 85 mm, 60 to 65 mm, or another suitable length. The length of the syringe barrel is the length between the rear end to the outlet to which the needle is attached (but not including the needle, if present).

The syringe barrel may have an internal diameter of 4 to 6.5 mm. If the syringe has a nominal maximum fill volume of 1 ml, the internal diameter of the syringe barrel may be 5.5 to 6.5 mm. If the syringe has a nominal maximum fill volume of 0.5 ml, the internal diameter of the syringe barrel may be 4 to 5 mm.

The wall of the syringe barrel may have a thickness of at least 1 mm; about 1 to 3 mm; about 1.5 to 3 mm; or about 2.4 to 2.8 mm. Due to the thickness of the wall, the sterilizing gas is restricted or prevented from entering interior of the syringe, thereby minimizing or preventing contact with the liquid formulation contained within the prefilled syringe.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a pre-filled syringe. The pre-filled syringe may have a maximum fill volume, i.e. a volume which can be maximally taken up by the syringe, of 0.3 ml to 1.5 ml, preferably of 0.5 ml to 1.0 ml. The volume of the liquid composition filled into the syringe may be about 0.05 ml to 1.0 ml; about 0.1 ml to 0.5 ml; about 0.14 ml to 0.3 ml; or about 0.15 ml to 0.2 ml. Syringes are typically filled with a larger volume than the volume actually administered to the patient to take into account any dead space within the syringe and the needle and the loss due to the preparation of the syringe for injection. Therefore, the volume which is actually administered to the patient may be between 0.01 ml and 1 ml; between 0.02 and 0.5 ml; between 0.025 and 0.5 ml; between 0.03 ml and 0.05 ml; or 0.05 ml.

In some embodiments, the reservoir of the pre-filled syringe includes a VEGF antagonist. For example, the VEGF antagonist may be a non-antibody VEGF antagonist. The term "VEGF antagonist" refers to a molecule which specifically interacts with VEGF and inhibits one or more of its biological activities, e.g. its mitogenic, angiogenic and/or vascular permeability activity. It is intended to include both anti-VEGF antibodies and antigen-binding fragments thereof and non-antibody VEGF antagonists. Non-antibody VEGF antagonists include aflibercept, pegaptanib and antibody mimetics. The non-antibody VEGF antagonist can be a VEGF-Trap. Preferably, the non-antibody VEGF antagonist is aflibercept. Aflibercept which is presently marketed under the name Eylea® and which is also known as VEGF-trap is a recombinant human soluble VEGF receptor fusion protein in which portions of human VEGF receptors 1 and 2 extracellular domains are fused to the Fc portion of human IgGI (Holash et al. (2002) Proc. Natl. Acad. Sci. USA 99(17): 11393-11398; WO 00/75319 Al; U.S. Pat. No. 7,070,959). Aflibercept comprises Ig domain 2 from VEGFR1 and Ig domain 3 from VEGFR2, fused to Fc domain of IgG1.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF). In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, biosimilars, variants or derivatives thereof: OPGL specific antibodies, peptibodies, related proteins, and the like (also referred to as RAN KL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP Ilb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4 integrin mAb); Valortim® (MDX-1303, anti-B. anthracis protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2 Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain a recombinant humanized IgG1 kappa isotype monoclonal antibody fragment designed for intraocular use, such as LUCENTIS® (ranibizumab). The drug delivery device may include a recombinant humanized monoclonal IgG1 antibody that contains human framework regions and murine complementarity-determining regions, such as AVASTIN® (bevacizumab). The drug delivery device may include a humanized monoclonal single-chain Fv (scFv) antibody fragment, such as BEOVU® (brolucizumab-dbll), or be used with a sclerostin antibody, such as but not limited to romosozumab, blosozumab, or BPS 804/setrusumab (Mereo) and in other embodiments, a monoclonal antibody (IgG) that binds human Proprotein Convertase Subtilisin/

Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. An injection device comprising:
  a syringe having a barrel and a flange; and
  a backstop configured to be coupled with the syringe adjacent to the flange during use of the syringe for drug delivery, the backstop having an inner surface including a C-shaped portion extending around at least a portion of a circumference of the syringe for an entire length of the C-shaped portion, wherein the C-shaped portion of the inner surface is interrupted by an opening that permits the backstop to receive the flange and/or the barrel, wherein the C-shaped portion of the inner surface further includes at least one protrusion extending away from the C-shaped portion of the inner surface, and wherein, upon coupling the syringe with the backstop, the at least one protrusion is configured to engage the flange and/or the barrel to create a space between the flange and/or the barrel and the C-shaped portion of the inner surface and to permit or promote airflow through the space between the C-shaped portion of the inner surface and the flange and/or the barrel, the backstop further having a cavity for receiving at least a portion of the flange, the cavity defined by opposing surfaces to limit axial movement of the backstop.

2. The injection device as in claim 1, wherein the at least one protrusion includes at least two protrusions.

3. The injection device as in claim 2, wherein the at least two protrusions includes at least three protrusions.

4. The injection device as in claim 3, wherein the at least three protrusions includes at least four protrusions.

5. The injection device as in claim 4, wherein the at least four protrusions includes at least five protrusions.

6. The injection device as in claim 5, wherein the at least five protrusions includes at least seven protrusions.

7. The injection device as in claim 1, wherein the inner surface of the backstop extends around at least a portion of the barrel of the syringe and the at least one protrusion engages the barrel of the syringe.

8. The injection device as in claim 1, wherein the backstop includes a collar portion defining the inner surface generally extending around at least a portion of the barrel.

9. The injection device as in claim 8, wherein the collar portion is configured to engage the syringe in a snap-fit relationship.

10. The injection device as in claim 1, wherein the barrel defines an axis and the at least one protrusion is a rib extending generally parallel with the axis.

11. The injection device as in claim 1, wherein the inner surface of the backstop includes the opposing surfaces defining the cavity and the at least one protrusion extends away from at least one of the opposing surfaces.

12. The injection device as in claim 11, wherein the opposing surfaces include a top opposing surface and a bottom opposing surface, the at least one protrusion includes at least one protrusion on the top opposing surface and at least one protrusion on the bottom opposing surface.

13. The injection device as in claim 12, wherein the at least one protrusion on the top opposing surface includes at least two ribs on the top opposing surface and the at least one protrusion on the bottom opposing surface includes at least two ribs on the bottom opposing surface.

14. The injection device as in claim 1, wherein the syringe is a pre-filled syringe containing a medicament.

15. The injection device as in claim 14, wherein the medicament comprises a VEGF antagonist.

16. The injection device as in claim 15, wherein the VEGF antagonist comprises a non-antibody VEGF antagonist.

17. The injection device as in claim 15, wherein the VEGF antagonist comprises a VEGF-Trap.

18. The injection device as in claim 17, wherein the VEGF-Trap comprises an aflibercept.

19. A packaging assembly comprising:
  a syringe having a barrel and a flange;
  a backstop configured to be coupled with the syringe adjacent to the flange during use of the syringe for drug delivery; and
  a packaging configured to receive an entire length of the syringe coupled with the backstop while physically supporting at least a portion of the syringe, wherein the packaging includes a cavity surface including a C-shaped portion and at least one protrusion disposed on the C-shaped portion of the cavity surface and extending away from the C-shaped portion of the cavity surface, and wherein the at least one protrusion is configured to engage the barrel of the syringe upon the syringe being disposed within the packaging to create a space between the syringe and at least a bottom portion of the C-shaped portion of the cavity surface and to permit or promote airflow through the space between at least the bottom portion of the C-shaped portion of the cavity surface and the syringe.

20. The packaging assembly as in claim 19, wherein the at least one protrusion includes at least two protrusions.

21. The packaging assembly as in claim 20, wherein the at least two protrusions are configured to engage the syringe in a snap-fit relationship.

22. A packaging assembly comprising:
a syringe having a barrel, a plunger rod at least partially received within the barrel, and a flange;
a backstop configured to be coupled with the syringe adjacent to the flange during use of the syringe for drug delivery; and
a packaging configured to receive an entire length of the syringe coupled with the backstop while physically supporting at least a portion of the syringe, wherein the packaging includes a cavity surface defining at least one raised wall section configured to engage the plunger rod of the syringe and resist and/or limit movement of the plunger rod, the cavity surface of the packaging further includes a C-shaped portion and at least one protrusion disposed on the C-shaped portion of the cavity surface and extending away from the C-shaped portion of the cavity surface, and wherein the at least one protrusion is configured to engage the barrel of the syringe upon the syringe being disposed within the packaging to create a space between the syringe and at least a bottom portion of the C-shaped portion of the cavity surface and to permit or promote airflow through the space between at least the bottom portion of the C-shaped portion of the cavity surface and the syringe.

23. An injection device comprising:
a syringe having a barrel and a flange; and
a backstop configured to be coupled with the syringe adjacent to the flange during use of the syringe for drug delivery such that axial movement of the backstop is limited by the backstop, the backstop having an inner surface including a C-shaped portion extending around at least a portion of a circumference of the syringe for an entire length of the C-shaped portion, wherein the C-shaped portion of the inner surface is interrupted by an opening that permits the backstop to receive the flange and/or the barrel, wherein the C-shaped portion of the inner surface further includes at least one protrusion extending away from the C-shaped portion of the inner surface, and wherein, upon coupling the syringe with the backstop, the at least one protrusion is configured to engage the flange and/or the barrel to create a space between the flange and/or the barrel and the C-shaped portion of the inner surface and to permit or promote airflow through the space between the C-shaped portion of the inner surface and the flange and/or the barrel such that only the at least one protrusion contacts the flange and/or the barrel of the syringe.

24. The injection device as in claim 23, wherein the inner surface of the backstop extends around at least a portion of the barrel of the syringe and the at least one protrusion engages the barrel of the syringe.

25. The injection device as in claim 23, wherein the backstop includes a collar portion defining the inner surface generally extending around at least a portion of the barrel.

26. The injection device as in claim 25, wherein the collar portion is configured to engage the syringe in a snap-fit relationship.

27. The injection device as in claim 23, wherein the barrel defines an axis and the at least one protrusion is a rib extending generally parallel with the axis.

* * * * *